United States Patent
Fleming et al.

(10) Patent No.: US 9,113,848 B2
(45) Date of Patent: Aug. 25, 2015

(54) SURGICAL RETRIEVAL APPARATUS

(75) Inventors: Alistair Ian Fleming, Lower Cambourne (GB); Jennifer Rachel Gell, Cambridge (GB); Cormac O'Prey, Bishops Stortford (GB)

(73) Assignee: Covidien LP, Mansfield, MA (US)

( * ) Notice: Subject to any disclaimer, the term of this patent is extended or adjusted under 35 U.S.C. 154(b) by 1193 days.

(21) Appl. No.: 12/975,778

(22) Filed: Dec. 22, 2010

(65) Prior Publication Data

US 2011/0190782 A1 Aug. 4, 2011

Related U.S. Application Data

(60) Provisional application No. 61/301,085, filed on Feb. 3, 2010.

(51) Int. Cl.
*A61B 17/50* (2006.01)
*A61B 17/00* (2006.01)
*A61B 17/30* (2006.01)

(52) U.S. Cl.
CPC . *A61B 17/00234* (2013.01); *A61B 2017/00287* (2013.01); *A61B 2017/00557* (2013.01); *A61B 2017/00561* (2013.01); *A61B 2017/00858* (2013.01); *A61B 2017/306* (2013.01)

(58) Field of Classification Search
CPC ...... A61B 17/221; A61B 17/24; A61B 17/30; A61D 7/00; A61M 37/0069
USPC .......... 606/110–115, 127, 128, 106; 600/562, 600/564–567; 604/59–64, 327–328
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,927,427 A | 5/1990 | Kriauciunas et al. |
| 4,997,435 A | 3/1991 | Demeter |
| 5,037,379 A | 8/1991 | Clayman et al. |
| 5,074,867 A | 12/1991 | Wilk |

(Continued)

FOREIGN PATENT DOCUMENTS

| | | |
|---|---|---|
| DE | 8435489 | 12/1984 |
| DE | 3542667 | 6/1986 |

(Continued)

OTHER PUBLICATIONS

"Extension" and "Extending" defined. The Free Dictionary. Accessed Jan. 28, 2015.*

(Continued)

*Primary Examiner* — Victor Nguyen
*Assistant Examiner* — Rachel S Papeika

(57) ABSTRACT

A surgical retrieval apparatus includes an elongate tubular member having a drive rod slidably disposed therein. A support member is operably coupled to a distal end of the drive rod. A pouch is attached to the support member and has a closed end and an open end. The pouch is securely coupled to the support member.

7 Claims, 23 Drawing Sheets

(56) References Cited

U.S. PATENT DOCUMENTS

| | | | |
|---|---|---|---|
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,423,830 A * | 6/1995 | Schneebaum et al. ......... 606/115 |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,836,953 A | 11/1998 | Yoon |
| 5,853,374 A * | 12/1998 | Hart et al. ................. 600/562 |
| 5,895,392 A | 4/1999 | Riek et al. |
| 5,906,621 A | 5/1999 | Secrest et al. |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternström |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 * | 5/2002 | Richard ................. 606/114 |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,971,988 B2 * | 12/2005 | Orban, III ................. 600/104 |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 8,172,772 B2 * | 5/2012 | Zwolinski et al. ............ 600/562 |
| 2004/0097960 A1 | 5/2004 | Terachi et al. |
| 2004/0138587 A1 | 7/2004 | Lyons |
| 2005/0267492 A1 | 12/2005 | Poncet et al. |
| 2006/0052799 A1 | 3/2006 | Middleman et al. |
| 2006/0058776 A1 | 3/2006 | Bilsbury |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2008/0091078 A1 * | 4/2008 | Roth et al. .................... 600/204 |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300621 A1 | 12/2008 | Hopkins et al. |
| 2008/0312496 A1 | 12/2008 | Zwolinski |
| 2009/0082779 A1 | 3/2009 | Nakao |
| 2009/0192510 A1 | 7/2009 | Bahney |
| 2009/0240238 A1 | 9/2009 | Grodrian et al. |
| 2010/0000471 A1 | 1/2010 | Hibbard |

FOREIGN PATENT DOCUMENTS

| | | |
|---|---|---|
| EP | 2184014 | 5/2010 |
| FR | 1272412 | 9/1961 |
| WO | WO 93/15675 | 8/1993 |
| WO | WO 95/09666 | 4/1995 |
| WO | WO 2004/002334 A1 | 1/2004 |
| WO | WO 2005/112783 A1 | 12/2005 |

OTHER PUBLICATIONS

Chinese Office Action dated Dec. 19, 2013 in Chinese Application No. 201110035602.7.

* cited by examiner

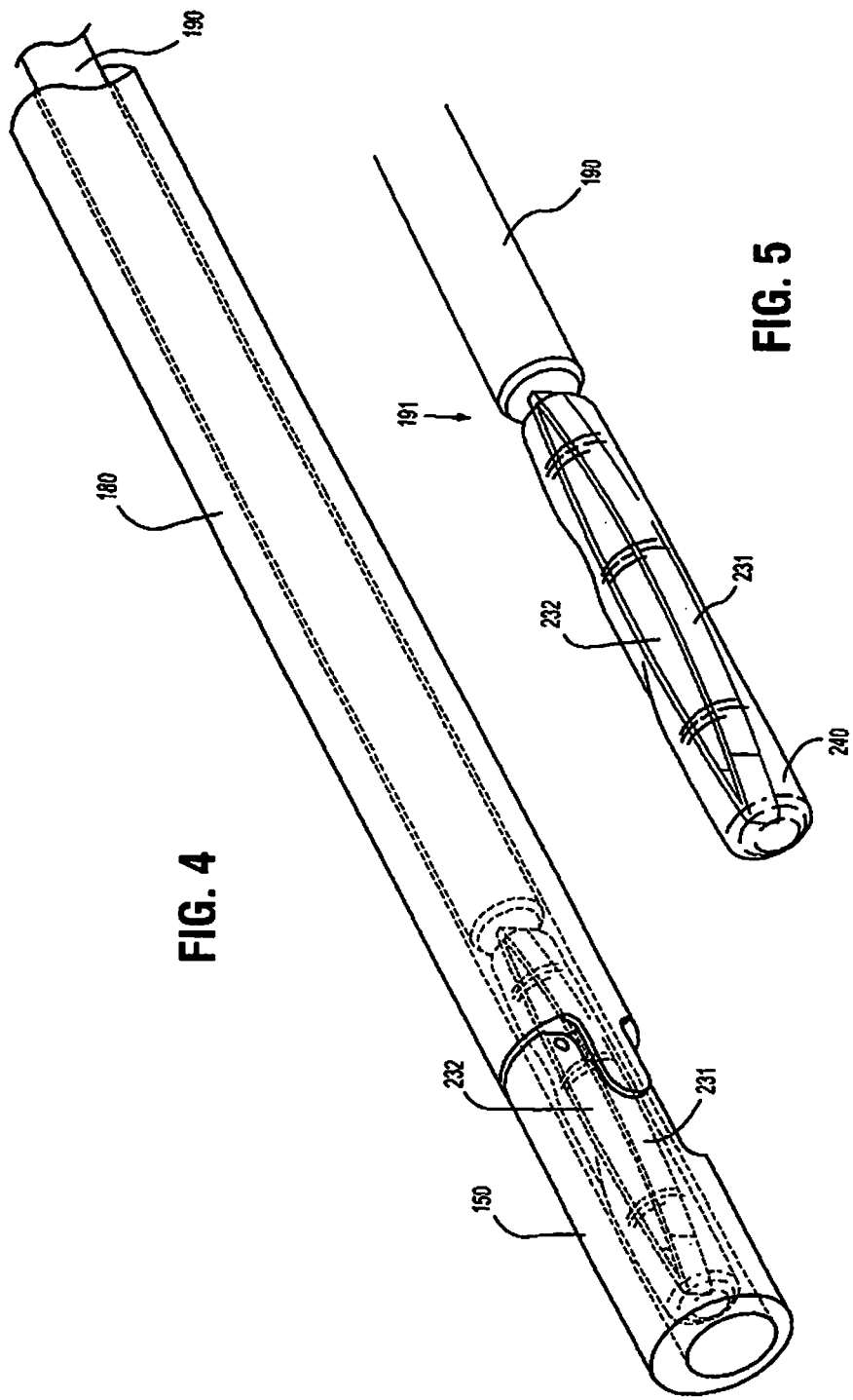

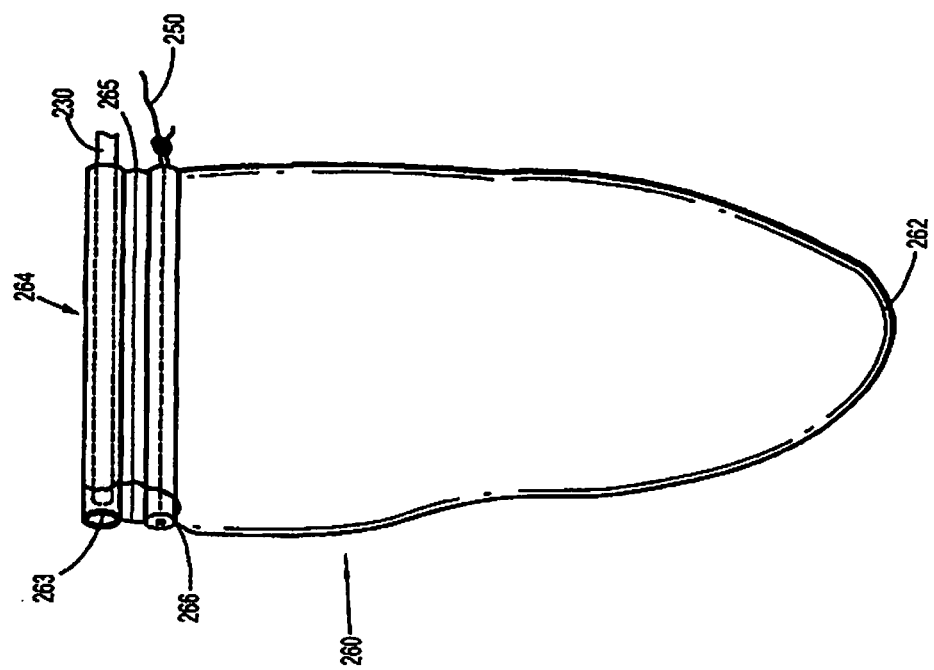

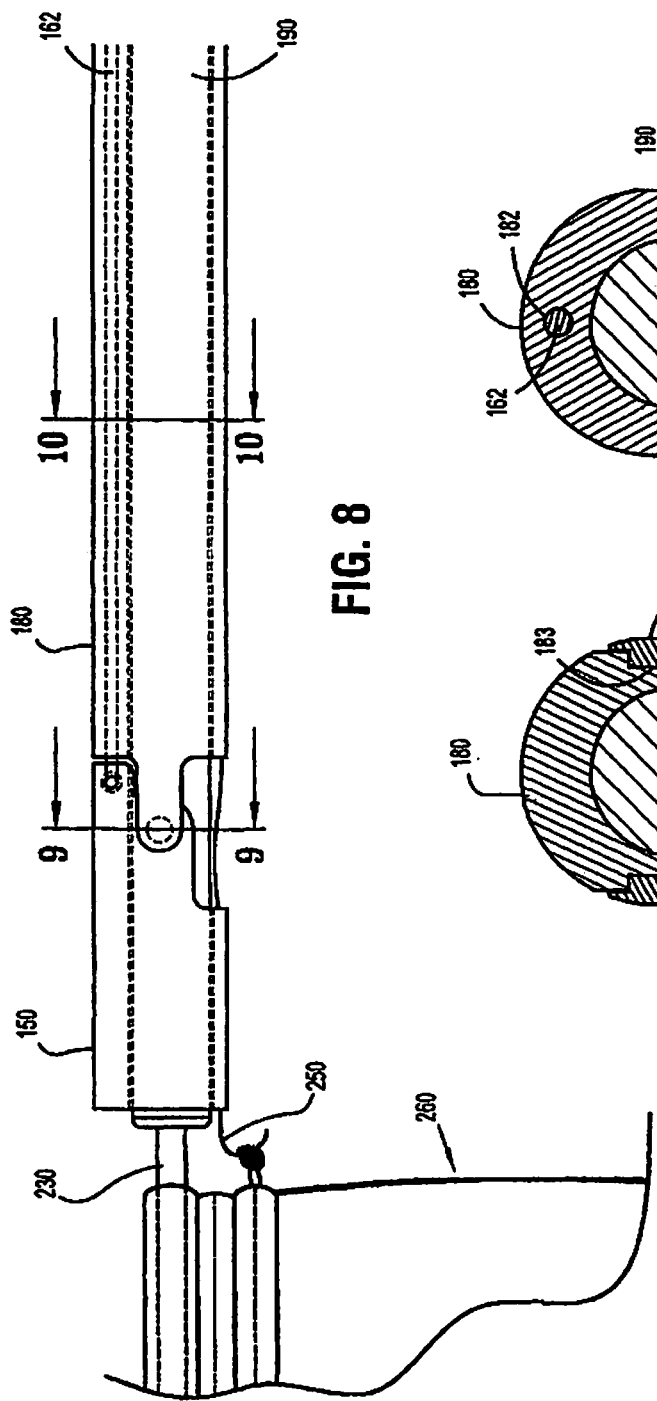

SURGICAL RETRIEVAL APPARATUS

CROSS-REFERENCE TO RELATED APPLICATIONS

This application claims priority from provisional application Ser. No. 61/301,085, filed Feb. 3, 2010, the entire contents of which are incorporated herein by reference.

BACKGROUND

1. Technical Field

The present disclosure relates to a surgical containment apparatus. More particularly, the present disclosure relates to a specimen retrieval apparatus and method for use in minimally invasive surgical procedures.

2. Background of Related Art

Laparoscopic and endoscopic surgical procedures are minimally invasive procedures in which operations are carried out within the body by using elongated instruments inserted through small entrance openings in the body. The initial opening in the body tissue to allow passage of the endoscopic or laparoscopic instruments to the interior of the body may be a natural passageway of the body, or it can be created by a tissue piercing instrument such as a trocar. Laparoscopic and endoscopic procedures generally require that any instrumentation inserted in the body be sealed, i.e. provisions must be made to ensure that gases do not enter or exit the body through the instrument or the entrance incision so that the surgical region of the body, e.g. the peritoneum, may be insufflated. Mechanical actuation of such instruments is for the most part constrained to the movement of the various components along a longitudinal axis with structure provided to convert longitudinal movement to lateral movement where necessary.

Because the endoscopic or laparoscopic tubes, instrumentation, and any required punctures or incisions are relatively narrow, endoscopic or laparoscopic surgery is less invasive as compared to conventional surgical procedures in which the surgeon is required to cut open large areas of body tissue. Therefore, laparoscopic or endoscopic surgery minimizes trauma to the patient and reduces patient recovery time.

Minimally invasive procedures may be used for partial or total removal of body tissue or organs from the interior of the body, e.g. nephrectomy, cholecystectomy, and other procedures including thoracic procedures. During such procedures, it is common that a cyst, tumor, or other affected tissue or organ must be removed via the access opening in the skin, or through a cannula. Various types of entrapment devices have been disclosed to facilitate this procedure. In many procedures where cancerous tumors are removed, removal of the specimen in an enclosed environment is highly desirable to prevent seeding.

U.S. Pat. No. 5,037,379 to Clayman et al. discloses a surgical tissue bag for percutaneously debulking tissue by morcellation. The bag includes a layer of puncture-resistant material, a layer of moisture-resistant material and a drawstring. In a disclosed method of use, the bag is placed within the body cavity, the body tissue or organ is placed within the bag, the opening of the bag is pulled through the incision in the skin leaving the distal end of the bag containing the tissue or organ within the body cavity, a morcellator is then inserted into the bag, and then the tissue or organ is debulked and suctioned out of the bag.

U.S. Pat. No. 5,074,867 to Wilk discloses a planar membrane having filaments attached to its corners. The membrane is placed within a body cavity with the filaments extending through the trocar cannula to the outside of the body. The organ or tissue to be removed is placed on the membrane and the filaments are pulled to close the membrane around the organ and draw it through the cannula, if the organ is sufficiently deformable. If the organ is not sufficiently deformable, e.g. because of the presence of gallstones, a forceps or other instrument is used to crush the stones or tissue.

Improvements to prior art entrapment devices are disclosed in U.S. Pat. No. 5,647,372 to Tovey et al. and in U.S. Pat. No. 5,465,731 to Bell et al., the disclosures of which are hereby incorporated by reference in their entirety. It would be advantageous to provide a retrieval device with increased maneuverability. Additionally, for certain procedures it might be advantageous to provide a retrieval device which reduces trauma to surrounding tissue.

SUMMARY

The present disclosure is directed to a surgical retrieval apparatus.

In one aspect, a surgical retrieval apparatus is provided including an elongated tubular member and a drive member slidably disposed in the elongated tubular member and having a first lumen in fluid communication with a fluid supply source operably associated with the surgical retrieval apparatus and a second lumen. A support member couples to the drive member and is movable between a proximal position and a distal position at least partially exterior to the elongated tubular member in response to axial movement of the drive member. The support member defines an internal chamber that includes a support channel and a fluid channel in fluid communication with the first lumen. The support member transitions from a first condition to a second condition when fluid is introduced into the fluid channel. A pouch extends from the support member and has a first end and a closed second end and a cavity defined therebetween. The first end is transitionable between open and closed configurations when the support member transitions between the first condition and the second condition. The cavity is in fluid communication with the second lumen such that the pouch compresses against a tissue specimen disposed within the pouch when air is evacuated from the cavity.

In some embodiments, the support channel and fluid channel are disposed adjacent to and in non-fluid communication with one another such that the support channel remains unpressurized during circulation of the fluid within the fluid channel. In some embodiments, the fluid channel is closed ended and the support channel is open ended.

In some embodiments, a support band is positioned within the support channel to provide an increased amount of structural integrity to the support member and the support band is substantially flexible and configured to flex under a predetermined amount of pressure applied thereto.

A vacuum tube can be provided including a vacuum head operably coupled to the second lumen and extending within the cavity of the pouch.

An interior surface of the pouch can be embossed and/or textured. The support member in some embodiments has an M-shaped configuration prior to introduction of fluid therein.

In another aspect, a surgical retrieval apparatus is provided comprising an elongated tubular member, a support member extending from the elongated tubular member and having a channel to receive fluid therein to expand the support member, and a pouch extending from the support member and movable to an open position upon expansion of the support member. The pouch includes a textured surface on an interior surface and an evacuation channel extending within the pouch and in fluid communication with the pouch to evacuate air from the pouch to collapse the pouch against a tissue specimen contained within the pouch.

A trigger mechanism can be provided actuable to introduce fluid into the channel of the support member. The support member can be substantially M-shaped in configuration prior to introduction of the fluid into the channel. The elongated portion can have an articulating distal portion.

In another aspect, a surgical retrieval apparatus is provided and includes an elongated tubular member having proximal and distal ends. A flange disposed at the distal end of the elongated tubular member defines a cavity therein. A drive member slidably disposed within the elongated tubular member is configured for axial movement within the elongated tubular member. A support member is movable between a retracted position and a distal position at least partially exterior to the flange when the drive member is moved axially. The support member is hinged to a distal end of the drive member. A pouch attached to the support member is movable therewith and includes a first end and a closed second end.

In some embodiments, the support member aligns with the at least two fingers when a tissue specimen is positioned within the pouch and the drive rod is moved to the retracted position. The fingers can be pivotably coupled to the support member. The flange can be spatula shaped.

In another aspect, a surgical retrieval apparatus is provided comprising an elongated tubular member, a drive member slidably disposed in the elongated tubular member, and a support member coupled to the drive member and movable between a proximal position and a distal position at least partially exterior to the elongated tubular member in response to axial movement of the drive member and movable between a first condition and a second expanded condition. A pouch extends from the support member and has a first end and a closed second end, the first end transitionable between open and closed configurations when the support member transitions between the first condition and the second condition, wherein air is evacuated from the pouch through the elongated tubular member to compress the pouch against a tissue specimen disposed within the pouch.

In some embodiments, the pouch includes a textured surface on an inner surface.

In some embodiments, the support member is substantially M-shaped in configuration prior to introduction of the fluid into the channel.

In some embodiments, the surgical retrieval apparatus further comprises a handle assembly including a vacuum port, the port communicating with a channel in the elongated tubular member. The support member can have a channel to receive fluid therein to expand the support member.

In some embodiments, a tube is positioned within the pouch adjacent the second end to evacuate air from the pouch.

In some embodiments, the elongated portion has an articulating distal portion.

BRIEF DESCRIPTION OF THE DRAWINGS

Embodiments of the presently disclosed specimen retrieval apparatus are described hereinbelow with reference to the drawings wherein:

FIG. 4 is a perspective view of a distal end of the specimen retrieval apparatus of FIG. 1 showing a support member coupled to a drive rod;

FIG. 5 is a perspective view of the spring and drive rod of FIG. 4 with a cover disposed about the support member;

FIG. 7 is a side view of the retrieval pouch of FIG. 6;

FIG. 8 is a side view of the distal end of the specimen retrieval apparatus of FIG. 1 with the retrieval pouch in the deployed state and the articulation assembly in a first state;

FIG. 9 is an end cross-sectional view taken along section line 9-9 of FIG. 8;

FIG. 10 is an end cross-sectional view taken along section line 10-10 of FIG. 8;

DETAILED DESCRIPTION OF THE EMBODIMENTS

Figure 1:
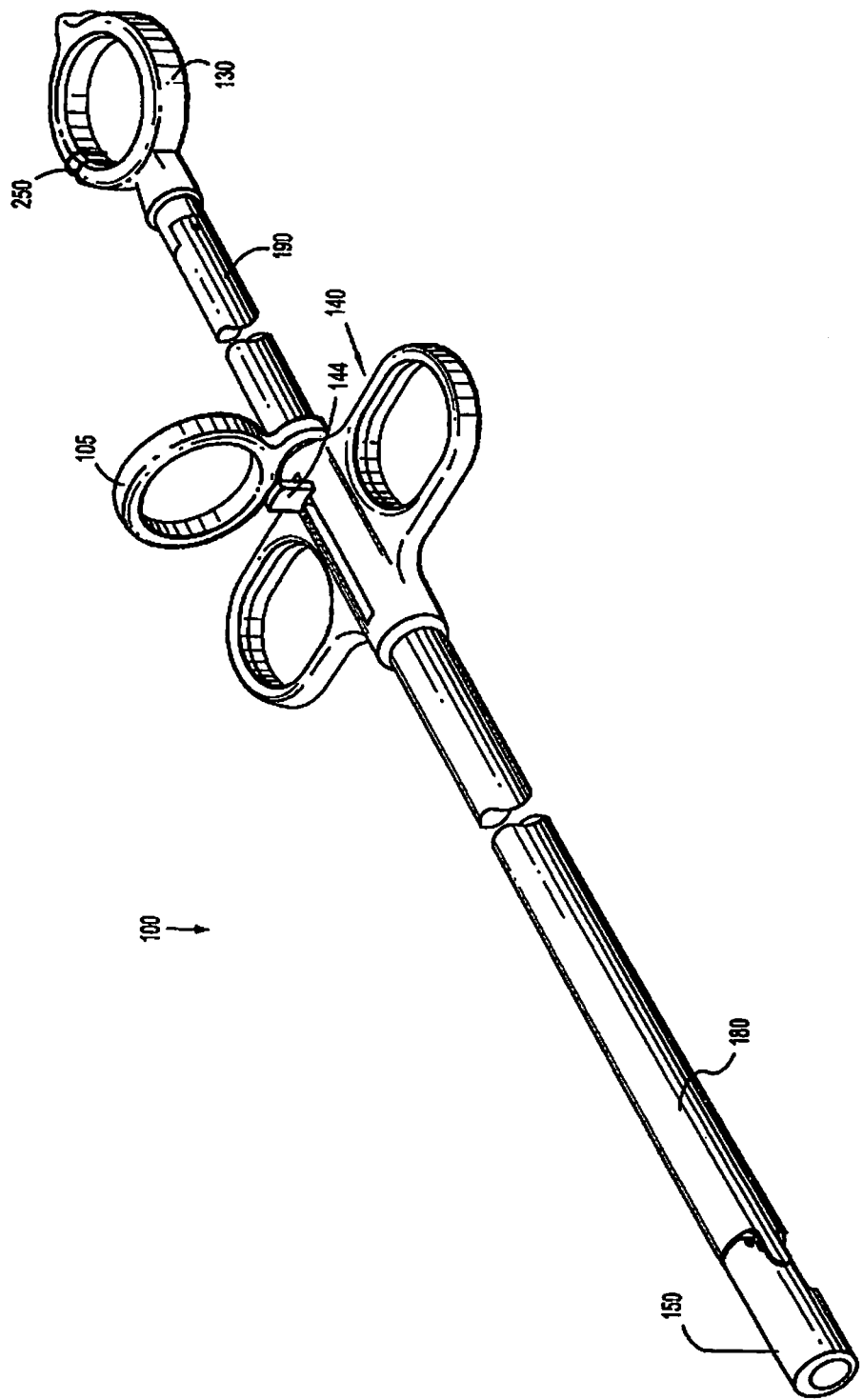
FIG. 1 is a perspective view of the specimen retrieval apparatus according to an embodiment of the present disclosure.

Embodiments of the present disclosure will now be described in detail with reference to the drawings, in which like reference numerals designate identical or corresponding elements in each of the several views. As used herein, the term distal refers to the portion of the instrument which is further from the user while, the term proximal refers to that portion of the instrument which is closer to the user. In the following description, well-known functions or constructions are not described in detail to avoid obscuring the present disclosure in unnecessary detail.

As used herein with reference to the present disclosure, the terms laparoscopic and endoscopic are interchangeable and refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula as in minimally invasive procedures. The devices herein may find particular use in minimally invasive thoracic surgery where access to the thoracic cavity is through a space located between adjacent ribs known as the intercostal space.

Figure 2:
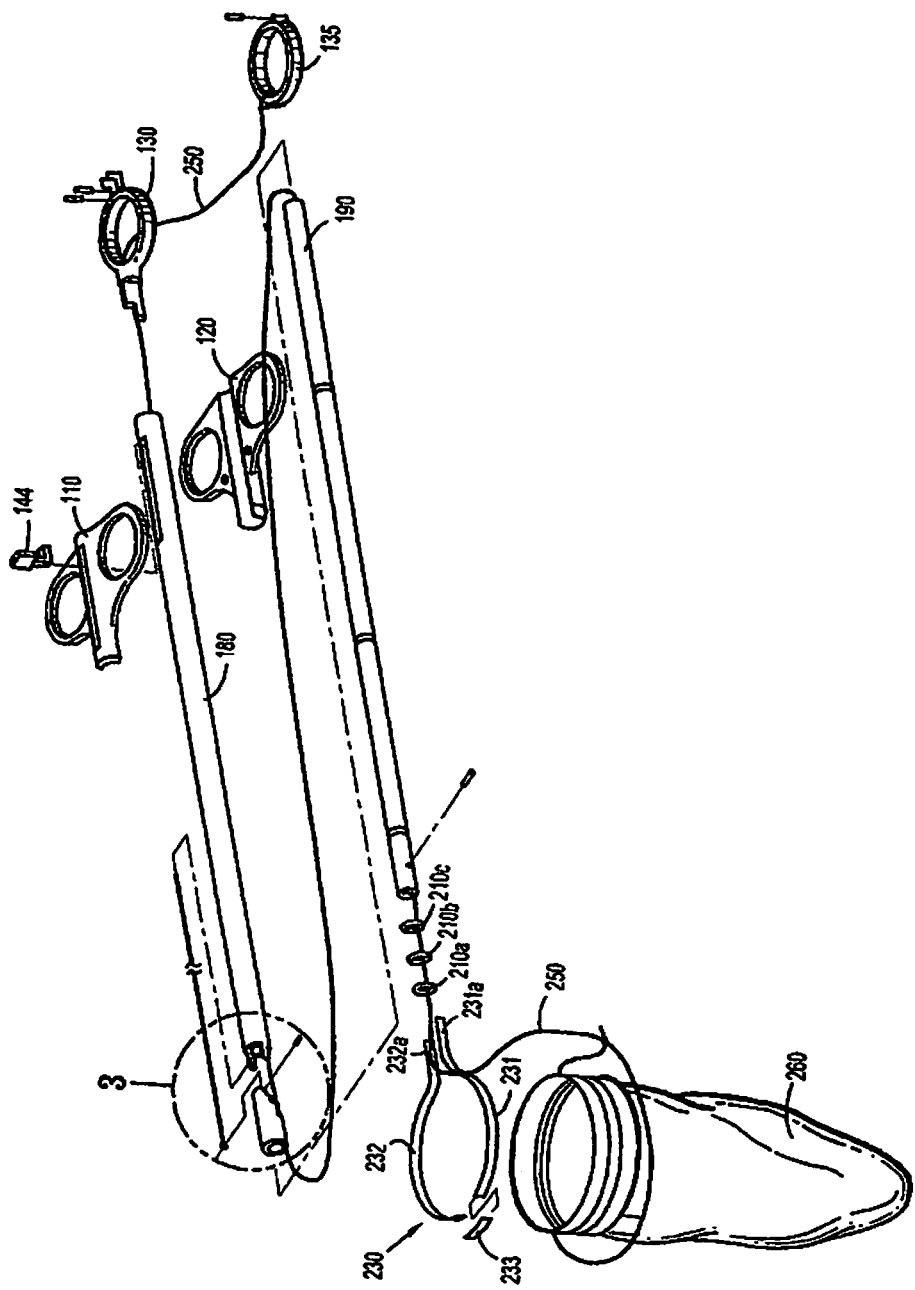
FIG. 2 is an exploded perspective view, with parts separated, of the specimen retrieval apparatus of FIG. 1.
Figure 3:
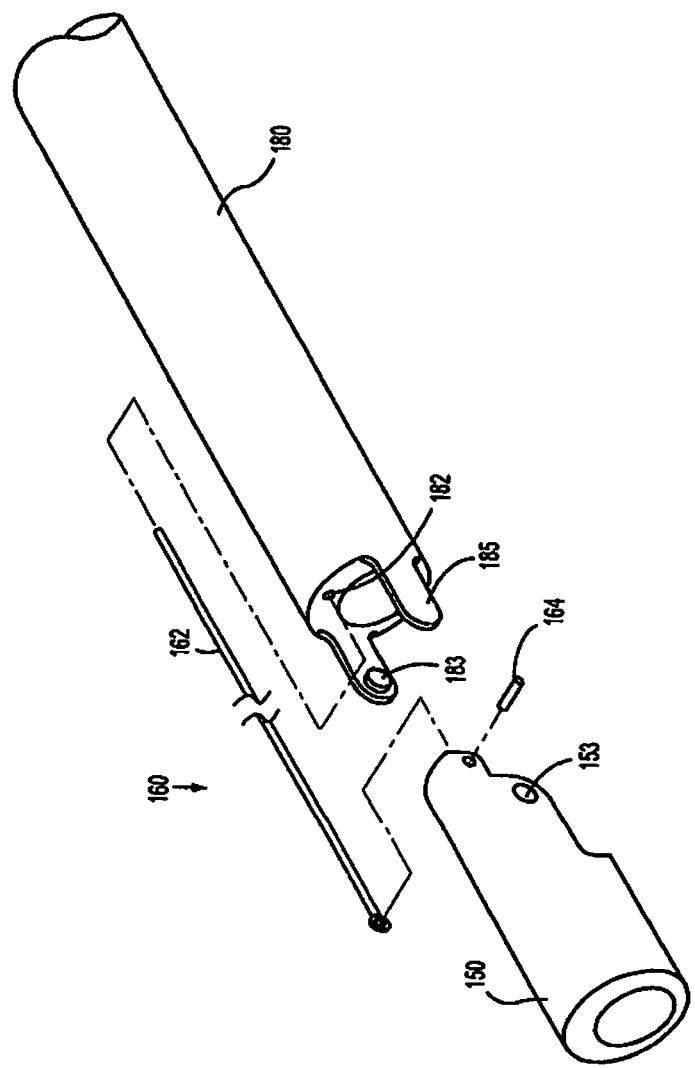
FIG. 3 is an enlarged view of detail area "3" in FIG. 2 illustrating an articulation assembly.

Referring initially to FIGS. 1 and 2, a surgical retrieval apparatus 100 is illustrated. Surgical retrieval apparatus 100 is preferably configured and dimensioned for use in minimally invasive surgical procedures (e.g. laparoscopic, endoscopic, and thoracic procedures). Surgical retrieval apparatus 100 includes an elongated tubular member 180, a handle 140, a finger loop 130 for engagement by a user's finger, a drive rod 190, and an end effector 150. Handle 140 includes handle portions 110, 120 and a slidable switch 144. In one embodiment, end effector 150 is coupled to a distal end of tubular member 180 using an articulation assembly 160 (FIG. 3) that will be described in detail below.

One end of a drawstring 250 is attached to finger loop 130, as shown in FIG. 2, while an opposing end of the drawstring 250 is attached to the pouch assembly 260 (FIGS. 2 and 7). In particular, the proximal end of drawstring 250 is attached to ring portion 135 that is releasably coupled to finger ring 130. Drawstring 250 is positioned within a lumen 186 of tubular member 180 (FIGS. 9 and 10). Tubular member 180 slidably houses drive rod 190 and, when undeployed, a pouch support or support member 230 and a pouch 260 (see FIG. 2). Support member 230 includes a resilient spring formed from support arms 231, 232. In the initial, unused condition, pouch 260 will be rolled up and the support member 230, including support portions 231, 232, will be relatively straight and positioned within tubular member 180 (FIGS. 4 and 5). When the drive rod 190 is advanced distally, support member 230 exits the distal end of tubular member 180 and resiliently pops open, thereby deploying and opening pouch 260 attached thereto.

Figure 6:
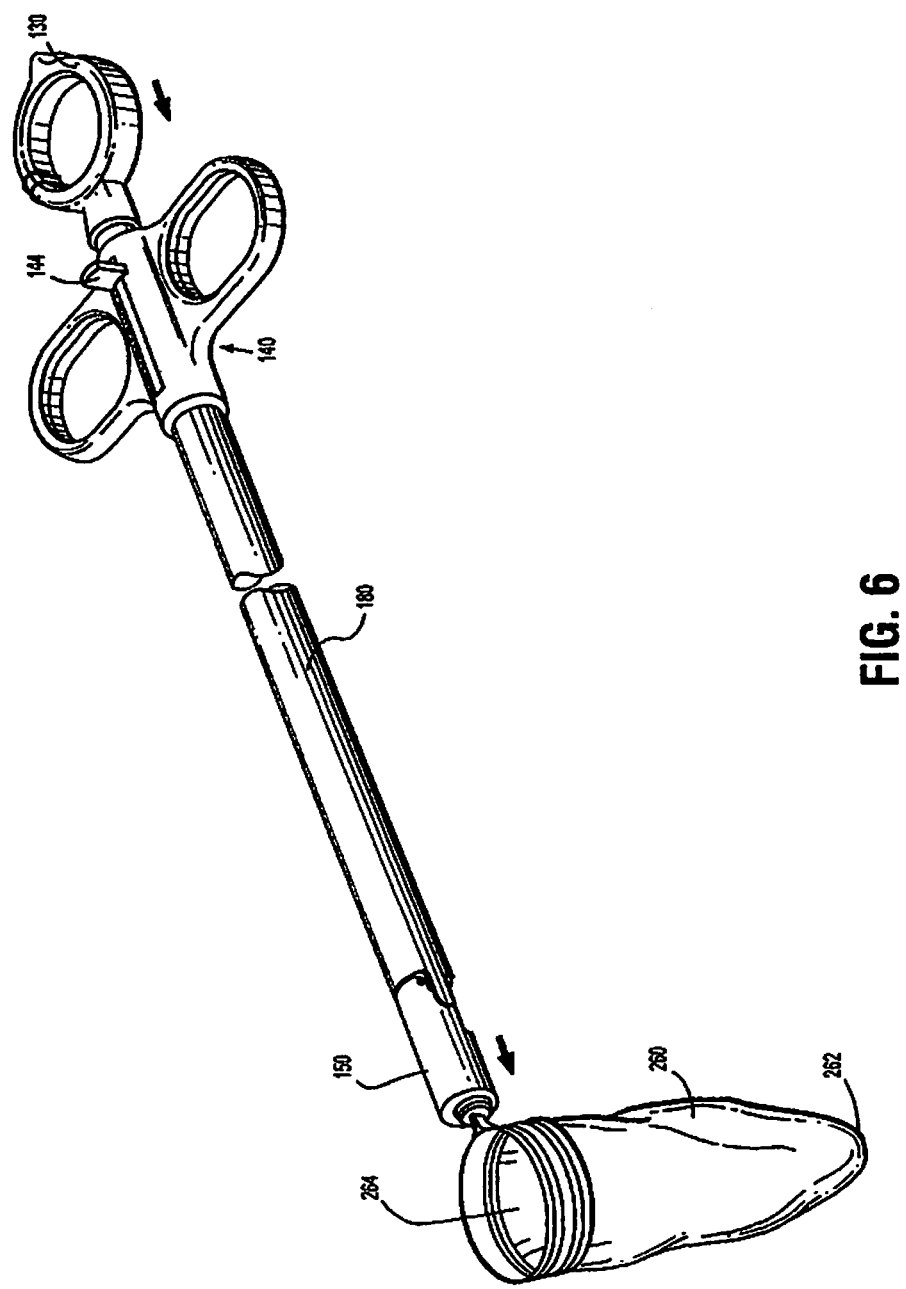
FIG. 6 is a perspective view of the specimen retrieval apparatus of FIG. 1 with a retrieval pouch in a deployed state.
Figure 13:
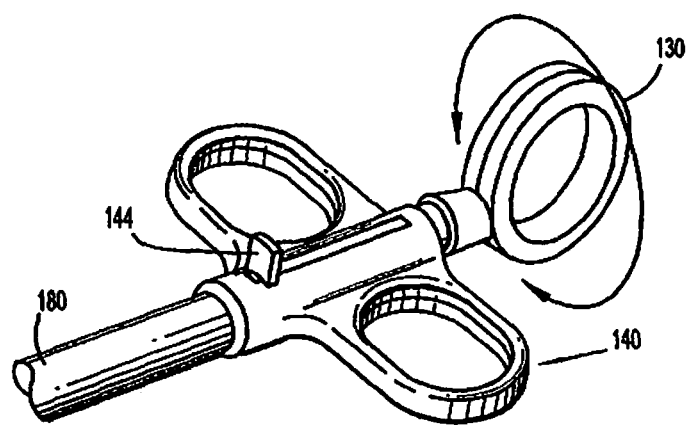
FIG. 13 is a perspective view of the handle of FIG. 11 with a finger loop rotated.
Figure 14:
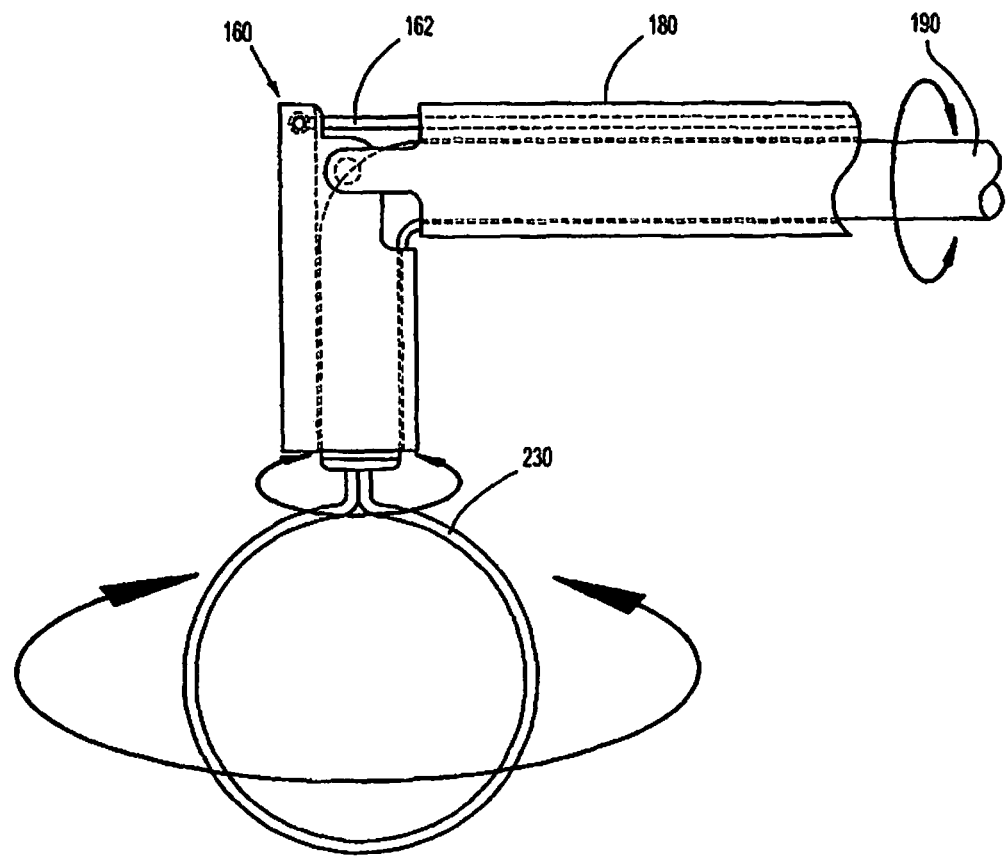
FIG. 14 is a side view of the distal end of the specimen retrieval apparatus of FIG. 1 with the articulation assembly in a second state and illustrating rotation of a support member assembly.

Drive rod or bar 190 is an elongated generally cylindrical member slidably disposed through the bore of tubular member 180. A distal end 191 of drive rod 190 is attached to pouch 260 to move pouch 260 from a non-deployed (retracted) position contained within the outer tubular member 180 (FIG. 4) to a deployed (advanced) position distal to the outer tubular member 180 (and end effector 150) (FIG. 6). Drive rod 190 also includes O-rings 210a, 210b, and 210c to help maintain a drawstring in place while permitting sliding movement of drive rod 190 through tubular member 180. In minimally invasive procedures utilizing insufflation, O-rings 210a-210c help maintain a gaseous seal. In the embodiments illustrated and described that include articulation assemblies and/or flexible portions, at least a portion of drive rod 190 is also flexible. Further still, drive rod 190 is rotatable about the longitudinal axis of tubular member 180 (FIG. 14) in response to rotation of finger loop 130 (FIG. 13) which rotates support member 230 and pouch 260.

A locking tab 105 can be included to prevent premature actuation of the surgical retrieval apparatus 100 during shipping. Locking tab 105 includes snap fit engagement structure to engage a slot of the drive rod 190. When thus engaged, drive rod 190 cannot be pushed distally beyond the point where locking tab 105 engages the proximal end of handle portions 110, 120. To actuate surgical retrieval apparatus 100, the surgeon first disengages locking tab 105 by pulling it off surgical retrieval apparatus 100.

Referring to FIG. 7, pouch 260 includes a flexible film or sheet formed from a substantially transparent polymeric material. Pouch 260 may be formed from a polyurethane sheet, although other biocompatible materials capable of forming a flexible membrane, such as latex, may be used. In one embodiment, pouch 260 is formed from an aromatic polyester type thermoplastic polyurethane such as Dureflex®, a product of Deerfield Urethane, Inc. in Whately, Mass. In addition, the material should be impervious to penetration by cancer cells. In certain embodiments, pouch 260 may be formed from an embossed and/or textured material, described in greater detail below or an embossed or textured surface can be applied to the bag during manufacture.

The pouch 260 may be of any dimensions suitable for the purpose of organ entrapment or removal. Pouch 260 includes a closed distal end portion 262 and an openable and closable end portion or mouth 264. Pouch 260 may alternatively include a circumferential concave portion in the vicinity of the open proximal end portion or mouth 264, for facilitating rolling and placement of the pouch 260 within tubular member 180 (FIG. 4). As seen in FIG. 5, a cover 240 can be used to enclose support member 230 and pouch 260 when they are loaded within tubular member 180. Open proximal end portion or mouth 264 is defined by a proximal (upper) circumferential tubular portion or sleeve 263, and a distal (lower) circumferential tubular portion or sleeve 266, which are spaced apart from each other.

Pouch 260 possesses a linear portion 265 weakened by perforation or scoring, which extends circumferentially around mouth 264 of pouch 260 between proximal and distal sleeves 263 and 266, respectively. Scored line 265 may be created by induction heating to create a linear portion having thickness less than that of the original material to facilitate tearing of the material along scored line 265.

Proximal sleeve 263 is adapted to receive support member 230. Distal sleeve 266 is adapted to receive drawstring 250 and extends circumferentially around mouth 264 of pouch 260 forming a loop or pathway for drawstring 250. One end of drawstring 250 may include a knot. Scored line 265 is adapted to tear when drawstring 250 is pulled with sufficient force to close mouth 264 of pouch 260 distal to scored line 265, thereby providing fast detachment of pouch 260 from support member 230 simultaneously with closure of mouth 264. Clearly, alternative structures also can be utilized to detach pouch 260 from support member 230, such as by pulling with a grasper or by cutting with a scissors.

Support member 230 includes two flexible and resilient support portions or arms 231, 232 as discussed above, which, in an unstressed or freely expanded condition, combine to form a generally circular hoop for supporting the periphery of mouth 264 of pouch 260 (in the open configuration). A joiner 233 (FIG. 2) is attached to the distal ends of support portions 231, 232. The distal ends of support portions 231, 232 meet in an opposing relationship where they are attached to each other by joiner 233. Joiner 233 may be a shrink tube. When force is applied to support member 230, support portions 231, 232 move toward each other in a substantially symmetrical manner. When support member 230 is stored inside tubular member 180 (FIG. 4), it is in the closed configuration. Support member 230 is resiliently biased towards the open configuration. Each support portion 231, 232 has a proximal end portion 231*a*, 232*a*, respectively, that are adapted to be received into an open end of drive rod 190. Longitudinal movement of drive rod 190 will move support member 230 and attached pouch 260 between the closed configuration and the open configuration. Support member 230 is preferably fabricated from a resilient metal (e.g. stainless steel).

Figure 11:
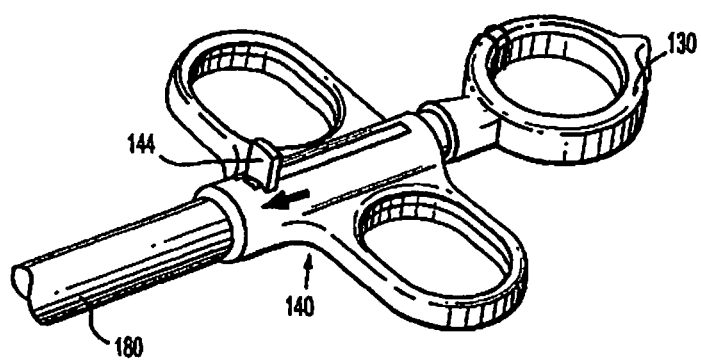
FIG. 11 is a perspective view of the handle of the specimen retrieval apparatus of FIG. 1 with an articulation switch in a second position.
Figure 12:
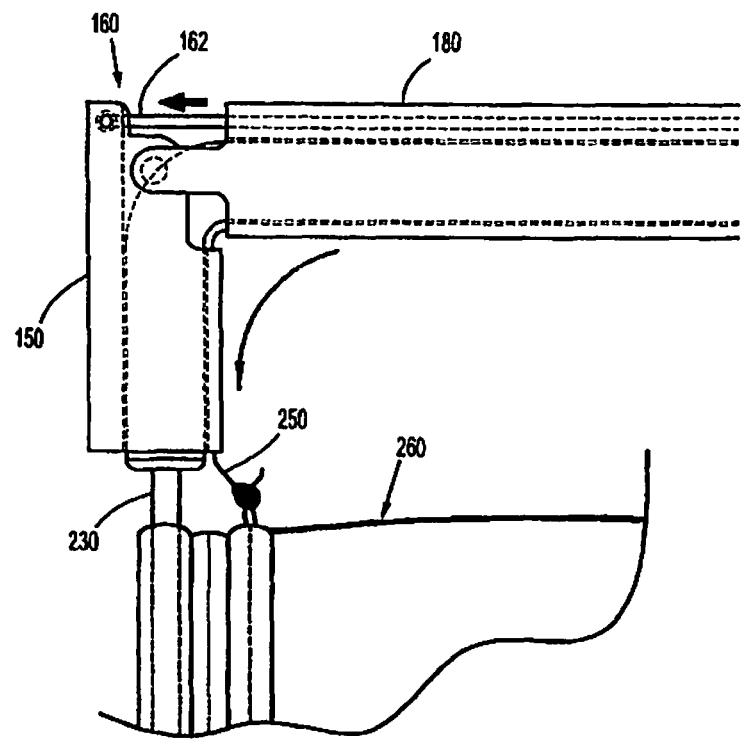
FIG. 12 is a side view of the distal end of the specimen retrieval apparatus of FIG. 8 with the articulation assembly in a second (articulated) state corresponding to the position of the switch in FIG. 11.

Referring now to FIGS. 2, 3, and 8-10, articulation assembly 160 includes a control arm 162. Control arm 162 is slidably disposed in a passage 182 of tubular member 180. A proximal end of control arm 162 is attached to switch 144 and a distal end is connected to end effector 150 via a pin 164. A pair of buttons 183 (FIG. 9) is located on inner surfaces of fingers 185 that extend distally from tubular member 180 (FIG. 8). A corresponding pair of openings 153 is located on end effector 150. When assembled, buttons 183 are rotatably disposed in openings 153 such that end effector 150 is pivotably coupled to tubular member 180. When switch 144 is in its proximal position (FIG. 1), control arm 162 maintains end effector 150 in substantial alignment with a longitudinal axis of tubular member 180. As switch 144 is slid towards its distal position (FIG. 11), it translates control arm 162 through passage 182 and repositions end effector 150 such that end effector 150 defines an angle with respect to the longitudinal axis of tubular member 180 (FIG. 12). Thus, end effector 150 is repositionable and defines a plurality of angles with respect to the longitudinal axis of tubular member 180 that ranges from about 0° to about 90°. In this manner, end effector 150 and pouch 260 are maneuverable, which allows the practitioner greater flexibility in performing a surgical procedure. Further still, end effector 150 includes a passage extending therethrough that is substantially aligned with the bore of tubular member 180.

Figure 17:
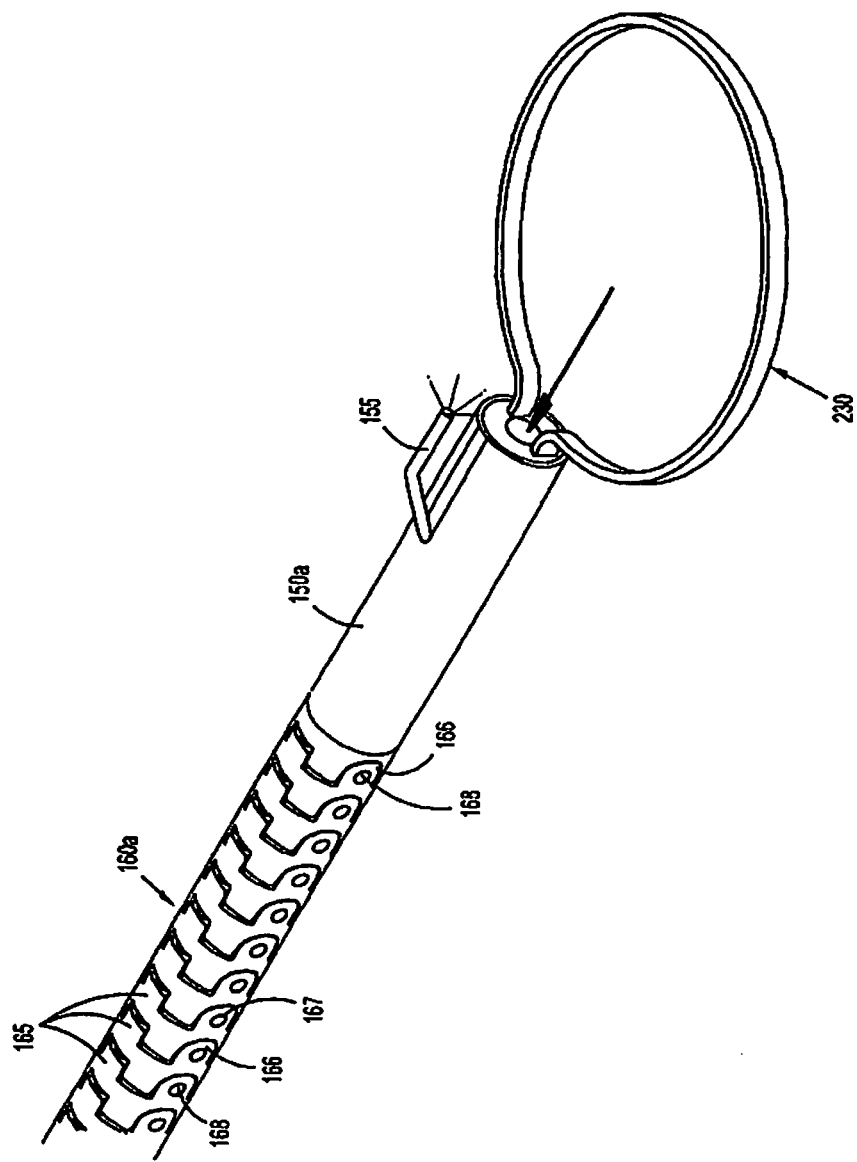
FIG. 17 is a perspective view of a distal end of an alternate embodiment of the presently disclosed specimen retrieval apparatus showing an alternative articulation assembly.

The surgical retrieval apparatus may include other articulation assemblies. Referring now to FIG. 17, an articulation assembly 160*a* is illustrated. In this embodiment, an end effector 150*a* is coupled to the distal end of tubular member 180 via articulation assembly 160*a*. Articulation assembly 160*a* includes a plurality of segments 165. Each segment 165 is pivotably coupled to an adjacent segment 165. In particular, each segment 165 includes a pair of opposed extensions 166 having openings 167 therein. Openings 167 rotatably receive posts 168 of the adjacent segment 165. A control arm (not shown), that is similar to control arm 162, extends through articulation assembly 160*a*. A proximal end of the control arm is attached to switch 144 and a distal end of the control arm is attached to an end effector 150*a*. End effector 150*a* is substantially similar to end effector 150 that was discussed above. End effector 150*a* differs in that a proximal end of end effector 150*a* includes a pair of posts 168 that are rotatably coupled to extensions 166 of segment 165. Further still, end effector 150*a* includes a tube 155 that is operator controllable for providing an irrigating fluid to the surgical site.

Figure 18:
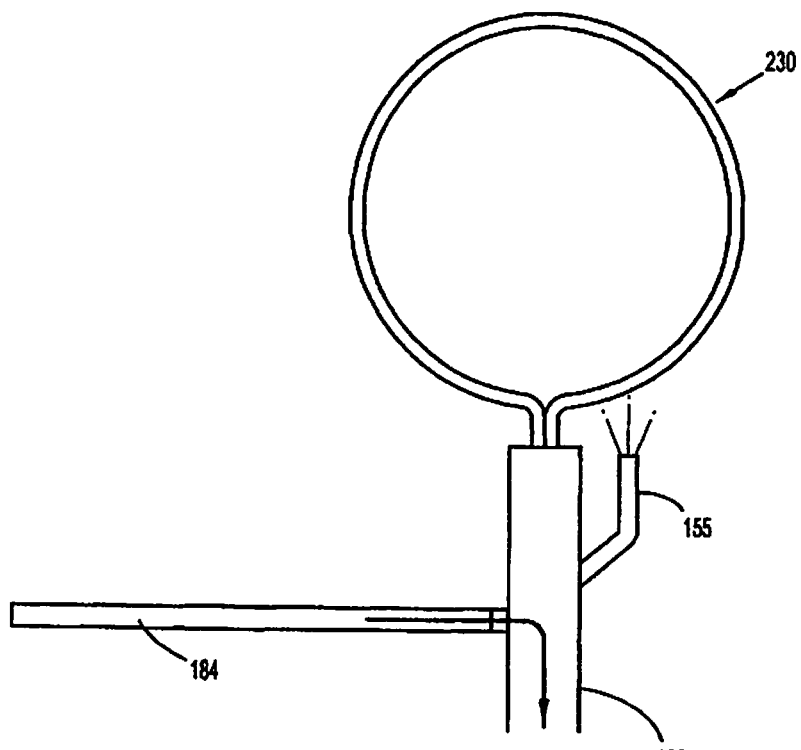
FIG. 18 is a side plan view of a further embodiment of the presently disclosed surgical retrieval apparatus depicting a vacuum line coupled to a distal end of the surgical retrieval apparatus.

In FIG. 18, a further embodiment of the surgical retrieval apparatus is shown. In this embodiment, an extension tube 184 is coupled to a distal end of tubular member 180. Extension tube 184 is directly attached to the exterior of tubular member 180 at the side as shown. Extension tube 184 is fluidly coupled to a source of vacuum (not shown) that is proximal to surgical retrieval apparatus 100. By supplying vacuum to the operative site, the practitioner is capable of removing small specimens or pieces of tissue in addition to capturing tissue specimens or samples in pouch 260. Further still, the vacuum supplied by extension tube 184 may be used to draw tissue specimens towards pouch 260 for facilitating retrieval of the tissue specimens. Tube 155 supplies an irrigating fluid to the surgical site and support member 230 can be rotatable about the longitudinal axis of tubular member 180 and articulatable with respect to tubular member 180 as in the embodiments described herein. It is contemplated that extension tube 184 may be flexible and/or articulable allowing the practitioner to maneuver the distal end of extension tube 184 to a desired location during the surgical procedure.

Figure 22:
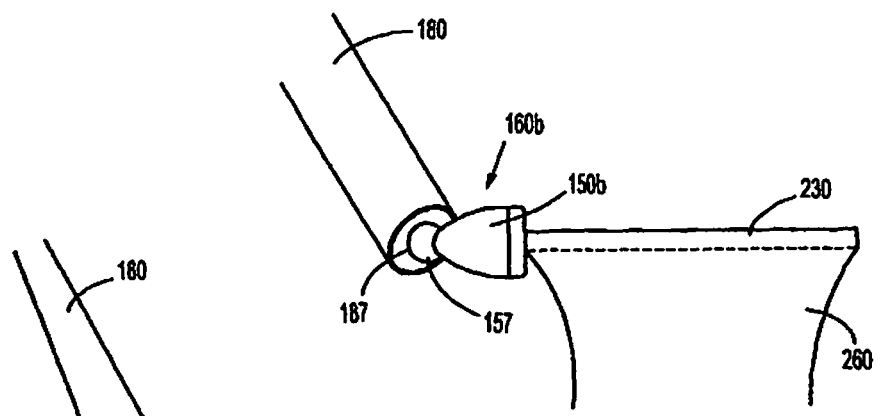
FIG. 22 is a perspective view of a distal end of yet another embodiment of the presently disclosed specimen retrieval apparatus illustrating an alternate articulation assembly.

Alternatively, as seen in FIG. 22, an articulation assembly 160*b* includes a socket 187 disposed at the distal end of tubular member 180 and a ball 157 attached to a proximal end of end effector 150*b*. End effector 150*b* is substantially similar to end effector 150 that was previously discussed and only the differences between them will be discussed in detail. In articulation assembly 160*b*, a control arm (not shown), that is substantially similar to control arm 162, is slidably disposed in tubular member 180. A proximal end of the control arm is attached to switch 144 and a distal end of the control arm is coupled to ball 157. In this arrangement, axial translation of the control arm rotates ball 157 in socket 187 thus repositioning end effector 150*b* relative to tubular member 180. Although not illustrated to scale, end effector 150*b* is configured and dimensioned to receive support member 230 and pouch 260 in their undeployed states. Further still, ball 157 includes a channel (not shown) for receiving an end of drive rod 190 that extends support member 230 from end effector 150*b* and retracts support member 230 into end effector 150*b*.

Figure 23:
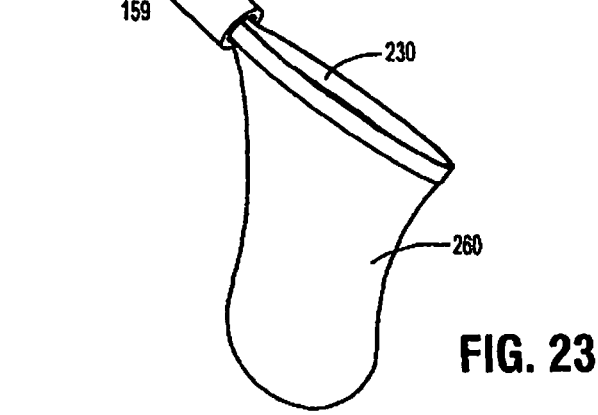
FIG. 23 is a perspective view of a distal end of a further embodiment of the presently disclosed specimen retrieval apparatus illustrating another articulation assembly.

Alternatively, as seen in FIG. 23, articulation assembly 160*c* includes a recess 189 formed at the distal end of tubular member 180 that rotatably receives a rounded end 159 of end effector 150*c*. End effector 150*c* is substantially similar to end effector 150 that was previously discussed and only the differences between them will be discussed in detail. Similar to articulation assembly 160*b*, a control arm extends through tubular member 180. A proximal end of the control arm is attached to switch 144 and a distal end of the control arm is coupled to a proximal end of rounded end 159. Axial movement of the control arm through tubular member 180 articulates end effector 150*c*. Recess 189 and rounded end 159 both have openings (not shown) for receiving a distal end of drive rod 190. As in previous embodiments, axial translation of drive rod 190 repositions support member 230 and pouch 260 between deployed and undeployed states.

Figure 24:
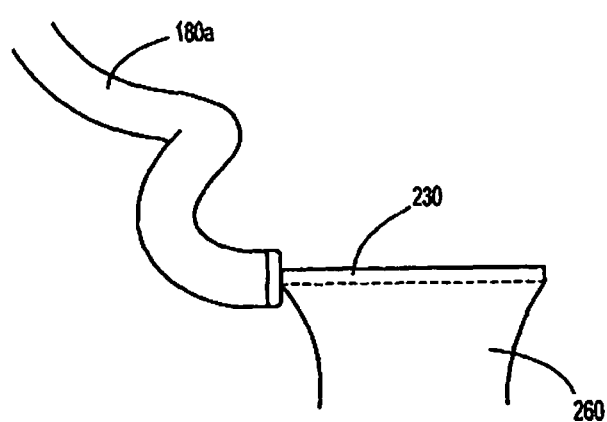
FIG. 24 is a perspective view of a distal end of an alternate embodiment of the presently disclosed specimen retrieval apparatus showing a flexible shaft.

Referring now to FIG. 24, tubular member 180*a* replaces tubular member 180 of previous embodiments. Tubular member 180*a* is substantially similar to tubular member 180, with only the differences between them being discussed in detail.

At least a portion of tubular member 180a is flexible allowing a distal end thereof to be repositioned in a variety of positions. It is contemplated that the flexible portion of tubular member 180a may be adjusted using a separate tool that is introduced through a separate access port. It is also envisioned that the flexible portion of tubular member 180a may be repositioned using one or more flexible cables disposed within tubular member 180a.

Figure 19:
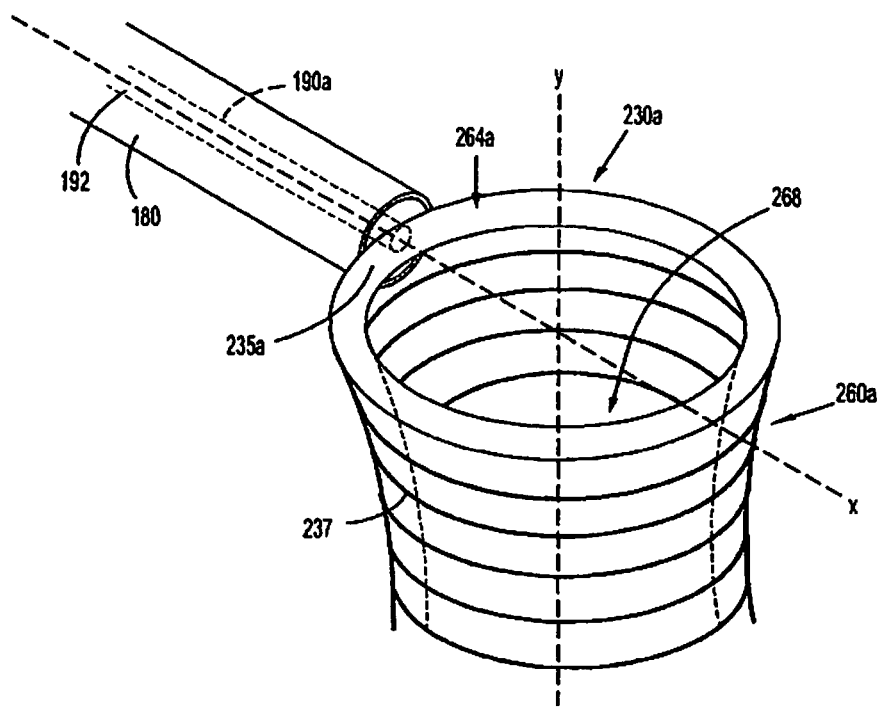
FIG. 19 is a perspective view of an alternate embodiment of a pouch for the presently disclosed surgical retrieval apparatus.

An alternative support member 230a is illustrated in FIG. 19. Support member 230a includes a chamber 235a and is coupled to a distal end of drive rod 190a. Drive rod 190a is substantially similar to drive rod 190 of previous embodiments, with only the differences being discussed in detail. In particular, drive rod 190a includes a central lumen 192 that is in fluid communication with chamber 235a of support member 230a and a source of fluid (not shown) at a proximal end of tubular member 180. Sources of fluid include pressurized gases (e.g. carbon dioxide) or liquids (e.g. saline). Other biocompatible fluids may be used as well.

Further still, support member 230a includes a plurality of splines 237 that are concentrically oriented and define a pouch 260a with a mouth 264a and a cavity 268. The pouch 160a has a closed end opposite the mouth 264a. In particular, support member 230a defines the pouch 260a when an inflation fluid is introduced into chamber 235a between inner and outer walls. Splines 237 provide structural support and help maintain orientation of support member 230a prior to the introduction of the inflation fluid (i.e. similar to support member 230 and pouch 260 of FIG. 4). In particular, support member 230a is an expandable member that is in fluid communication with a source of inflation fluid (not shown) via central lumen 192 of drive rod 190a. As support member 230a expands, it defines mouth 264a and pouch 260a which extends substantially transverse to a longitudinal axis of tubular member 180. Specifically, support member 230a expands substantially circumferentially about axis X, while expanding substantially transverse along axis Y. By providing surgical retrieval apparatus with support member 230a, a separate pouch 260 is not necessary.

Figure 20:
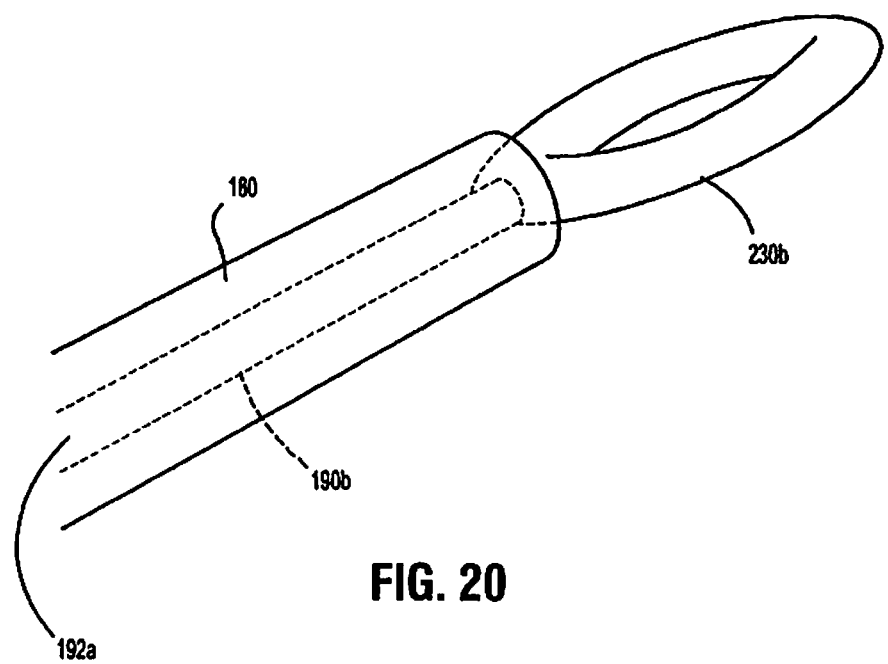
FIG. 20 is a perspective view of a distal end of an embodiment of the presently disclosed specimen retrieval apparatus illustrating an alternate support member assembly.

Referring now to FIG. 20, an alternate support member 230b is depicted. Support member 230b is an expandable ring having a chamber defined between inner and outer walls thereof. In this embodiment, support member 230b is coupled to a distal end of drive rod 190b and if desired can be configured to be movable between a retracted position within tube 180 and an advanced position extending from the tube 180. Alternately, in the deflated state, it can remain outside the tube 180. In this embodiment, when the practitioner desires to open the mouth of the pouch (not shown), the practitioner introduces the selected fluid into the chamber 235b via central lumen 192a. The fluid causes the support 230b to expand from a collapsed condition to an expanded condition (FIG. 20), thereby opening the mouth of the pouch which is supported by support 230b. The practitioner may also withdraw the fluid from the chamber causing support member 230b to contract and urging the mouth closed. It is envisioned that a source of vacuum may be placed in fluid communication with the chamber such that the practitioner may apply vacuum and cause the mouth to close completely. The expandable ring support member can reduce trauma to surrounding tissue. The inflatable ring allows the practitioner to control the amount of inflation and deflate support member 230b while the support member 230b is distally spaced from the distal end of tubular member 180. This allows the practitioner increased flexibility when performing surgical procedures. Support member 230b may also include one or more lengths of material for reinforcement similar to those employed in support member 230a. The reinforcing material (e.g. metal bands or threads) may be disposed within the chamber or may be incorporated into the walls of support member 230b. By including reinforcing material into the structure of support member 230b, the rigidity of support member 230b is increased while maintaining the flexibility.

Figure 21:
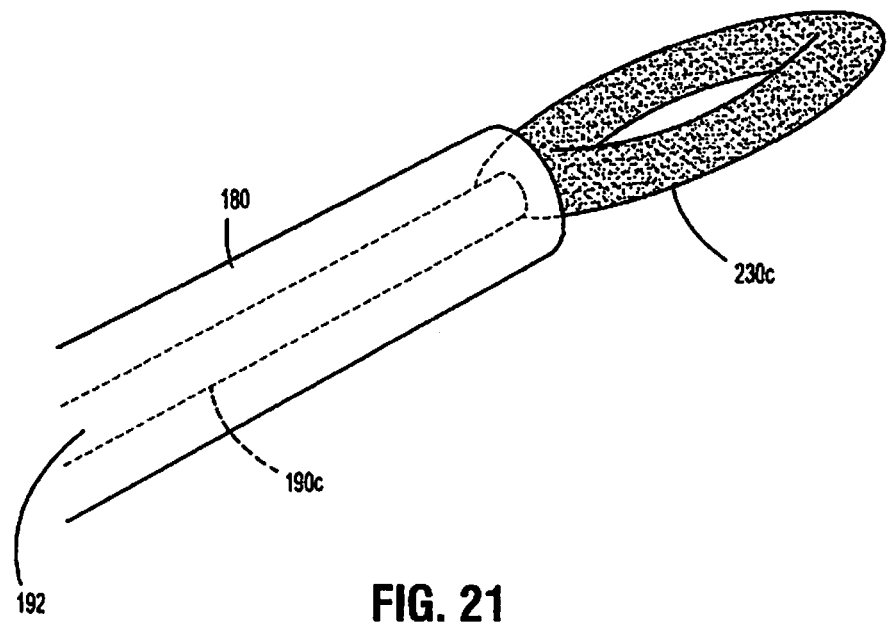
FIG. 21 is a perspective view of a distal end of an embodiment of the presently disclosed specimen retrieval apparatus illustrating another alternate support member assembly.

Referring now to FIG. 21, an alternate support member 230c is shown. Support member 230c is formed from an expandable foam material. Suitable biocompatible foams are known in the art. Support member 230c is biased towards the open or deployed condition as shown in FIG. 21. When support member 230c is located within tubular member 180, it is in the collapsed condition. Axial movement of drive rod 190c moves support member 230c from within tubular member 180 to a location distal of tubular member 180. Alternatively, in the non-expanded state it can remain outside tubular member 180. Similar to support member 230, as support member 230c exits the distal end of tubular member 180, its natural bias urges support member 230c towards the deployed condition. Alternatively, support member 230c may include a chamber that is coupled to a lumen of drive rod 190c. In this situation, the chamber is in fluid communication with a proximal end of drive rod 190c similar to that discussed hereinabove. This permits the practitioner to introduce a foam material into the chamber, which causes expansion of support member 230c. When using an external source of foam material, support member 230c does not expand to the deployed state upon exiting the distal end of tubular member 180. In this instance, the practitioner deploys support member 230c by axially translating drive rod 190 and subsequently introducing the foam material and expanding support member 230c. A foam material can in some instances provide a more rigid support member than using a gas as in support member 230b.

At times it may become necessary to remove tissue samples or other small amounts of tissue from a patient. Using known techniques, a surgeon makes one or more incisions in the patient's skin. A cannula or other access device is inserted in each of the incisions. The operative site may be insufflated with a biocompatible fluid (e.g. carbon dioxide) if increased space is desired such as in laparoscopic surgery. In other minimally invasive procedures, such as thoracic procedures, where access is provided between adjacent ribs, the cavity is not insufflated. The surgical retrieval apparatus, e.g. apparatus 100, is inserted through one of the cannulas and maneuvered towards the tissue sample to be retrieved. Once surgical retrieval apparatus 100 is in the vicinity of the tissue sample, the surgeon removes locking tab 105, if it has not been previously removed. The surgeon grasps finger ring 130 and moves drive rod 190 distally through tubular member 180. Distal movement of drive rod 190 moves support member 230 and pouch 260 through an open distal end of tubular member 180 and end effector 150. Once support assembly 230 clears the distal end of end effector 150, support assembly 230 opens causing mouth 264 of pouch 260 to open. The surgeon maneuvers pouch 260 towards the tissue sample to be retrieved. Depending on the circumstances, the surgeon may rotate pouch 260 by rotating finger ring 130. Also, the surgeon may reposition end effector 150 off axis by adjusting switch 144, which controls the articulation of end effector 150.

Figure 15:
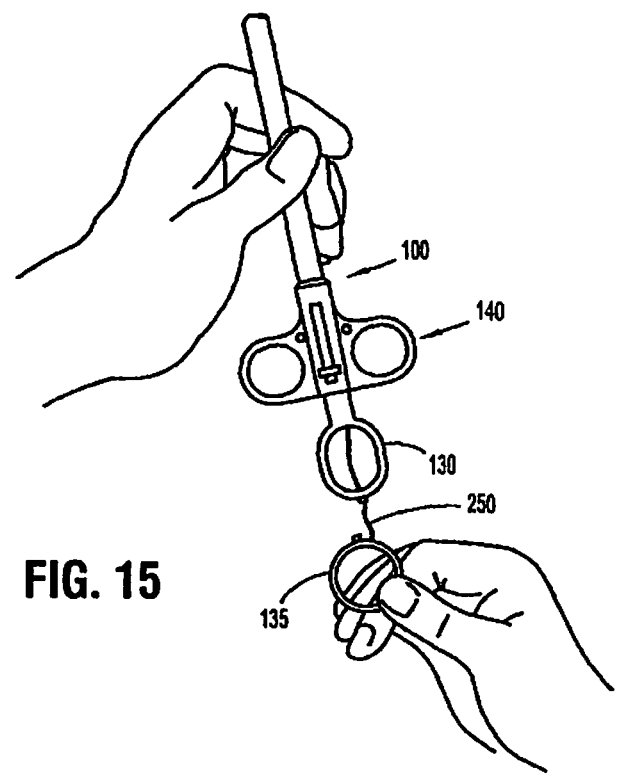
FIG. 15 illustrates cutting a drawstring of the specimen retrieval apparatus.
Figure 16:
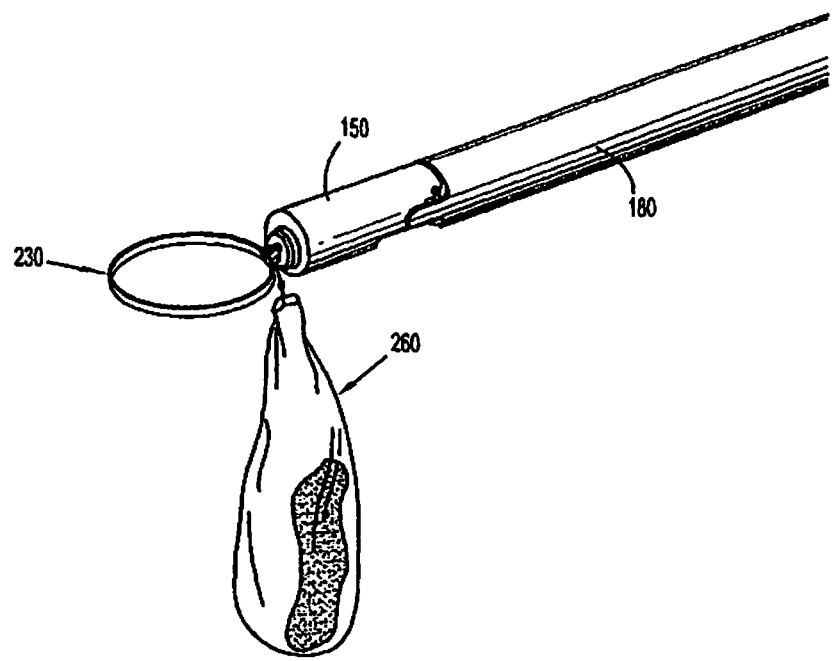
FIG. 16 is a perspective view of the distal end of the specimen retrieval apparatus of FIG. 1 with the retrieval pouch separated from the support member assembly.

Once the tissue sample is located within pouch 260, the surgeon closes mouth 264 by pulling drawstring 250 proximally using ring portion 135. Continued proximal movement of drawstring 250 also separates pouch 260 from support member 230 (FIG. 16). The surgeon cuts drawstring 250 using a knife that is mounted on finger ring 130 (FIG. 15). Through a separate access tube, the surgeon inserts a grasper for retrieving pouch 260. The surgeon grabs drawstring 250 near support assembly 230 and withdraws pouch 260 containing the tissue sample. Surgical retrieval apparatus 100 is then removed from the operative site.

When utilizing the other embodiments of the support assembly, the surgeon will place the pouch about the tissue sample as before. Since these embodiments do not include a drawstring, the surgeon will use other methods, such as a knife or other cutting tool to separate the pouch from the support assembly. In certain instances, the pouch can remain attached and the apparatus removed through the access port or opening.

Figure 25A:
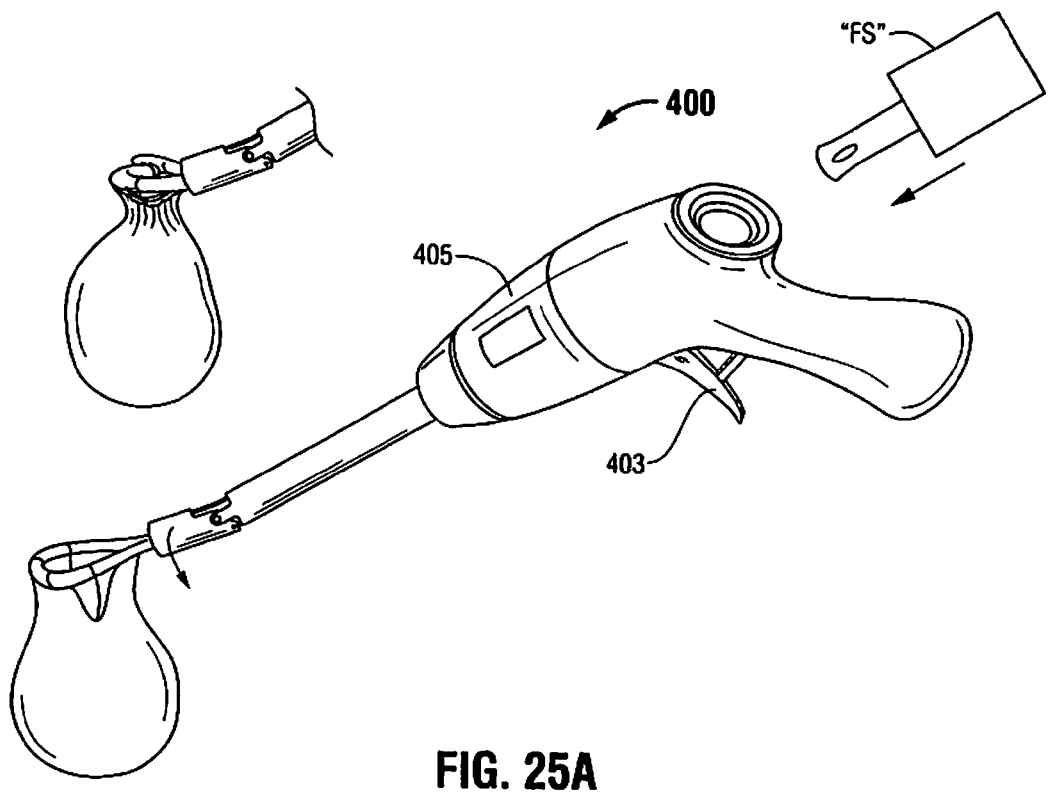
FIG. 25A is a perspective view of a further embodiment of the presently disclosed surgical retrieval apparatus.

With reference to FIGS. 25A-29E, and initially with reference to FIG. 25A, a further embodiment of the surgical retrieval apparatus is shown designated 400. In this embodiment, a fluid supply/evacuation device "FS," hereinafter simply referred to as "FS," operably couples to the surgical retrieval apparatus 400 and supplies and/or evacuates one or more suitable types of fluid, e.g., gas and/or liquid, to and/or from the surgical retrieval apparatus 400. More particularly, "FS" couples to a proximal end of the surgical retrieval apparatus 400, FIG. 25A. In one particular embodiment, "FS" couples to a portal that is located at the proximal end of the surgical retrieval apparatus. In certain instances, the portal may be tapered to accommodate a wide range of suction tubes that may be operably associated with "FS." One or more suitable intermediary interfaces (not shown), such as, for example, one or more lengths of tubing, are operably associated with the portal of the surgical retrieval apparatus and couples "FS" to a drive rod 401 (FIG. 27) associated with the surgical retrieval apparatus 400.

Drive rod 401 is operably associated with the surgical retrieval apparatus 400. Drive rod 401 is substantially similar to drive rod 190c and, so as not to obscure the present disclosure with redundant information, only those features that are unique to drive rod 401 are described in further detail. Drive rod 401 includes first and second lumens 402 and 404, respectively, that are in fluid communication with "FS," a support member 406 and a pouch 408 (shown schematically in FIG. 25B). Drive rod 401 is configured for axial movement within the elongated tubular member 180 (FIG. 25B) that is operably associated with the surgical retrieval apparatus 400, and is securely coupled to support member 406 (and/or operative components associated therewith) by one or more suitable coupling methods.

Support member 406 is in fluid communication with the first lumen 402 that is configured to inflate and/or deflate the support member 406. To this end, the support member 406 is made from one or more suitable types of inflatable material, such as, for example, an elastic material that is impervious to the fluid that circulates within support member 406. Support member 406 is generally circumferential in shape (when in the inflated or open configuration) and is configured to support pouch 408. Support member 406 is deployable from within the elongated tubular member 180. More particularly, when support member 406 is deployed from within the elongated tubular member 180, support member 406 includes a generally "M" shaped configuration, see FIG. 29A, for example, that enhances maneuverability and enables opening of the pouch 408 in a more confined space. Support member 406 is configured to transition from a substantially compressed or deflated state to an expanded or inflated state (or vice versa) to open the pouch 408. To this end, support member 406 defines an internal chamber or cavity that includes a fluid channel 412 (see FIG. 26, for example) that is in fluid communication with the first lumen 402. Support member also defines a support channel 410.

In the illustrated embodiment, the support channel 410 and fluid channel 412 are disposed adjacent to and in non-fluid communication with one another such that the support channel 410 remains unpressurized, thereby facilitating transition of the support member 406 from an expanded or inflated state to a substantially compressed or deflated state. That is, a pressure associated with a fluid that is introduced into the fluid channel 412 is not compromised during circulation thereof through the fluid channel. The support channel 410 and fluid channel 412 extend within the cavity of the support member 406, with the support channel being open ended and the fluid channel being close ended. More particularly, the support channel 410 extends along the length of the support member 406 and provides an egress back into the elongated tubular member 180 toward the drive rod 401. The fluid channel 412 extends to a predetermined location within the cavity of the support member 406. In the illustrated embodiment, fluid channel 412 extends substantially along the length of the support member 406. Note it is also contemplated that rather than two channels a single channel can be provided.

Support channel 410 is dimensioned to house a support rim or band 414 (FIG. 26) that is configured to provide an amount of structural integrity to the support member 406. In the illustrated embodiment, the support band is coupled to the drive rod 401. This configuration of having the support band coupled to the drive rod 410 facilitates deployment of the support member 406 from within the elongated tubular member 180. In certain embodiments, it may prove advantageous to have an end of the support member 406 coupled to the drive rod 401 and an end not coupled to the drive rod. Moreover, and in certain embodiments, it may prove advantageous to have the support band 414 operably disposed within the support channel 410 and not coupled to the drive rod 410. Support band 414 is substantially flexible and is configured to flex or "give" under a predetermined amount of force or pressure that is applied thereto. More particularly, when the support member 406 is in the inflated or expanded state, the support band 414 is in a normally non-flexed state, and when the support member 406 is in the deflated or compressed state, the support band 414 is in a flexed state. In the illustrated embodiment, support band 414 may be made from one or more suitable types of polymer that is capable of supporting the pouch 408 and capable of flexing when the pouch transitions from a non-compressed state to a compressed state. In the illustrated embodiment, support band 414 is made from an elastomeric material, such as, for example, a thermoplastic.

As with the previously described pouches, e.g., pouch (specimen retrieval bag) 260, pouch 408 includes a mouth 416, a cavity 418 and a closed end 420 opposite the mouth 416. Pouch 408 may be made from any of the previously described materials that were described with respect to pouch 260. Unlike the previously described pouches, e.g., pouch 260, that were removably coupled to their respective support members, e.g., support member 230, pouch 408 is securely coupled to the support member 406 by one or more suitable coupling or securement methods, e.g., an adhesive.

Figure 27:
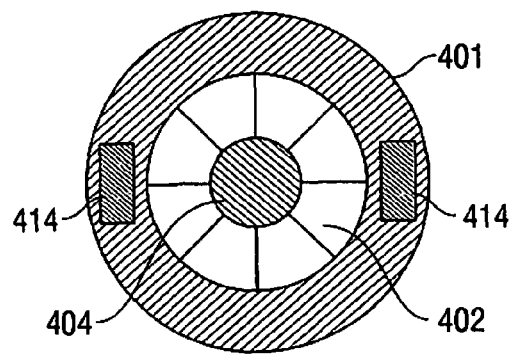
FIG. 27 is an end cross-sectional view taken along section line 27-27 of FIG. 25B.
Figure 28A:
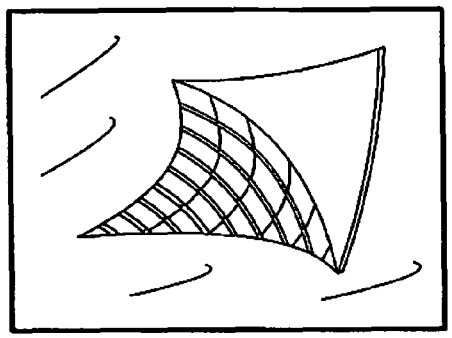
FIG. 28A is an enlarged view of detail area "28A" in FIG. 25B illustrating one type of surface that may line an interior of the pouch depicted in FIG. 25B.
Figure 28B:
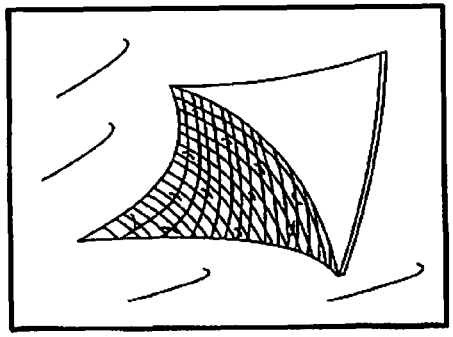
FIG. 28B is an enlarged view of detail area "28B" in FIG. 25B illustrating another type of surface that may line an interior of the pouch depicted in FIG. 25B.

In the embodiment illustrated in FIGS. 25A-28D, an interior surface 422 of the pouch 408 may be embossed (FIG. 28A) and/or textured (FIG. 27B). An interior surface 422 that is embossed and/or textured facilitates specimen removal and enhances fluid, e.g., air, removal or evacuation from the cavity 418. That is, to facilitate this air removal or evacuation from the cavity of pouch 408 including a specimen "S" contained therein, air is evacuated from the cavity 418 of the pouch 408 such that the pouch 408 forms a "shrink wrap" around the specimen "S." This reduces the volume of the bag to facilitate removal through the incision.

Figure 25B:
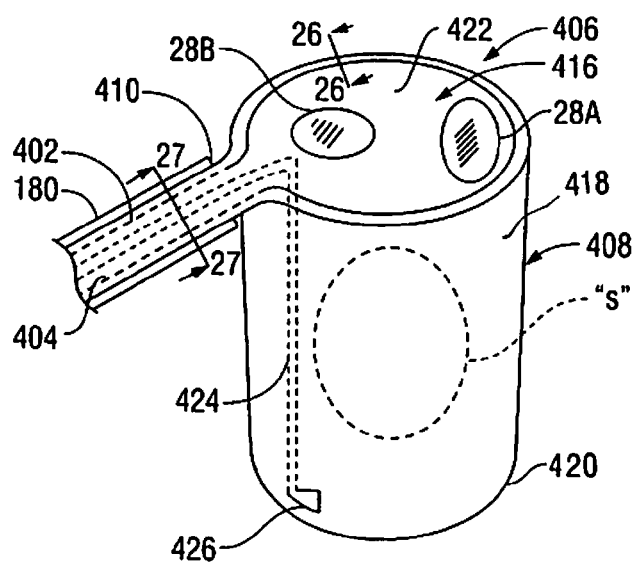
FIG. 25B an enlarged view of detail area "25B" in FIG. 25A illustrating a distal end of the surgical retrieval apparatus.
Figure 26:
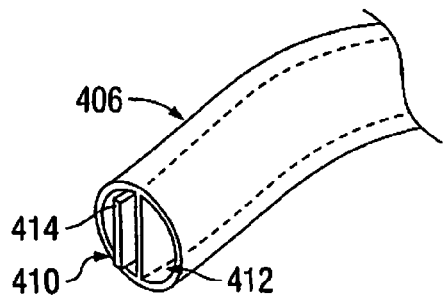
FIG. 26 is a partial cut-away view taken along section line 26-26 of FIG. 25B.

To remove or evacuate air from the cavity 418 of the pouch, one or more devices or structures operably couples to the second lumen 404 of drive rod 401 and is in fluid communication with the cavity 418 of pouch 408. More particularly, a vacuum tube 424 including a distal vacuum head 426 is operably coupled to the second lumen 404 and extends within the cavity 418 of the pouch 408. In the illustrated embodiment, vacuum head 426 is positioned adjacent the closed end 420 of the pouch 408 (FIG. 25B). Positioning the vacuum head 424 in the manner illustrated in FIG. 25B, facilitates evacuation of air from the cavity 418. Positioning the vacuum adjacent the closed end 412 can be advantageous when the pouch includes a textured surface as the vacuum head 24 can be spaced from the specimen which is held away from the bottom of the pouch by the gripping of the textured surface. Vacuum tube 424 including vacuum head 426 may made from any suitable material including, but not limited to those materials previously described herein with respect to pouch 408 and/or support member 406. While the second lumen 404 and vacuum tube 424 including vacuum head 424 have been described as being configured to remove fluid from the cavity 418, each of the foregoing components may be configured to introduce fluid into the cavity 418. This can be accomplished by simply reversing the flow of fluid from "FS."

Figure 29A:
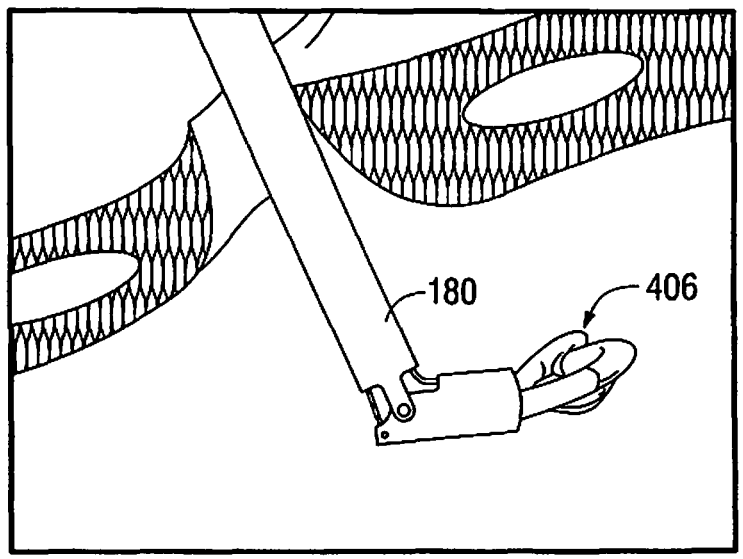
FIGS. 29A-29E illustrate steps associated with a method of use of the specimen retrieval apparatus depicted in FIG. 25A.
Figure 29B:
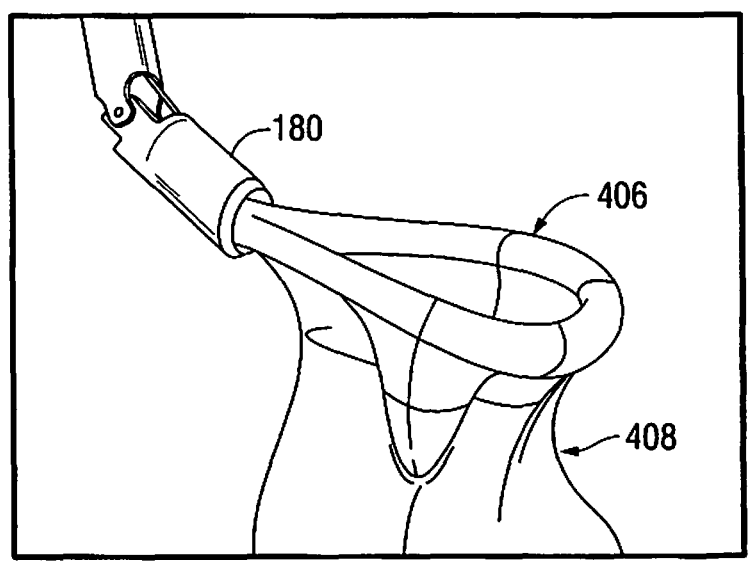
Figure 29C:
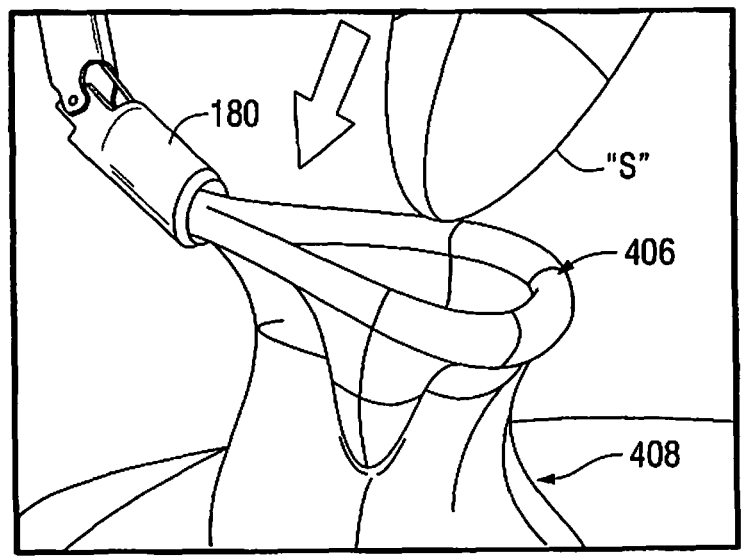
Figure 29D:
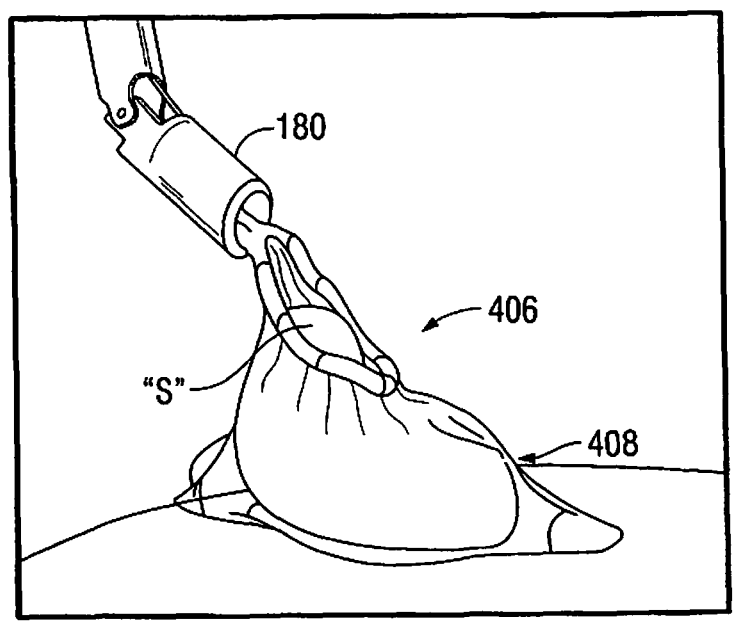
Figure 29E:
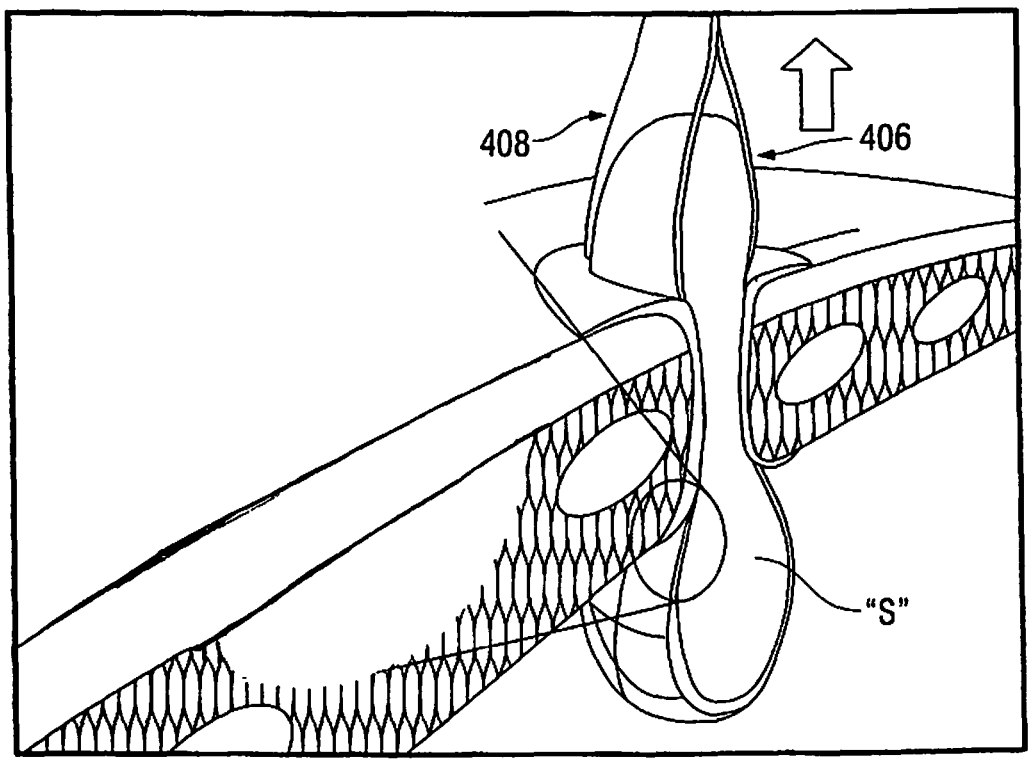

In use, elongated tubular member 180 is positioned within a thoracic cavity of a patient (FIG. 29A). Subsequently, support member 406 including pouch 408 is deployed from within the elongated tubular member 180 via a trigger mechanism 403 operably associated with the surgical retrieval apparatus as actuation of the trigger injects fluid into the support member 406. Initially, support member 406 is in a compressed state having a generally "M" shape. To inflate the support member 406 and open the pouch 408, fluid, e.g., air, from the source of fluid "FS" is introduced into the first lumen 402 and into fluid channel 412. In the illustrated embodiment, the source of fluid "FS" is controllable via one or more control mechanisms, e.g., a trigger 405, operably associated with the surgical retrieval apparatus 400. It is also contemplated that button 405 can be utilized to inject fluid and the trigger used to articulate the distal end as described below. Note articulation of the distal portion provides increased maneuverability of the pouch within the body cavity. After the support member 406 is inflated and the pouch 408 is opened (FIG. 29B), a tissue specimen is placed within the cavity 418 of the pouch 408 (FIG. 29C). Subsequently, air is removed from the fluid channel 412 of the support member 406, and from the cavity 418 via vacuum head 424, which, in turn, causes the pouch to form a shrink wrap around the specimen "S" (FIG. 29D). Thereafter, the elongated tubular member 180 including support member 406 and pouch 408 are removed from the cavity, e.g. the thoracic cavity (FIG. 29E). The textured surface on the interior of the pouch helps to prevent the specimen from sliding to the bottom of the pouch 408 and "balling" at the bottom. This facilitates removal through the incision, as the specimen shape can be better maintained for removal through the oval shaped incision.

Figure 30:
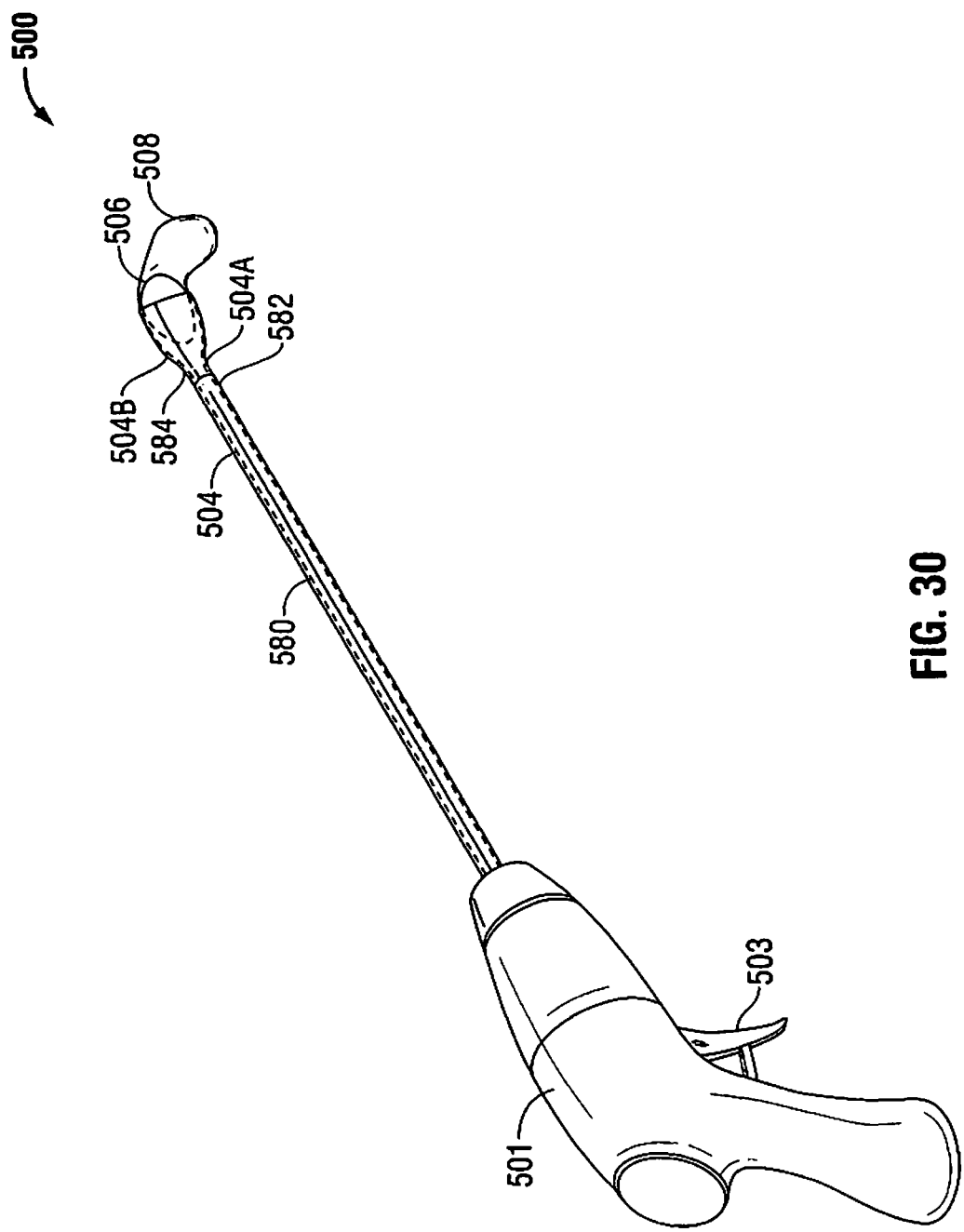
FIG. 30 is a perspective view of a distal end of an embodiment of the presently disclosed specimen retrieval apparatus illustrating an alternate support member assembly.
Figure 31A:
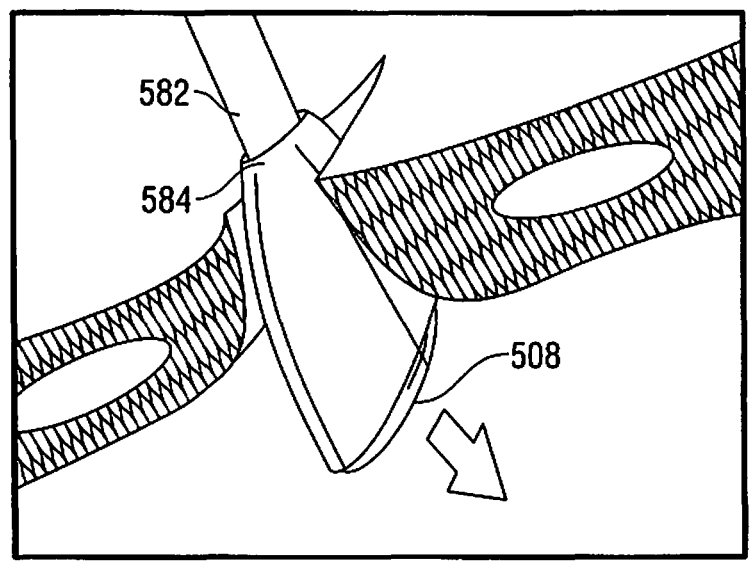
FIGS. 31A-31F illustrate steps associated with a method of use of the specimen retrieval apparatus depicted in FIG. 30.
Figure 31B:
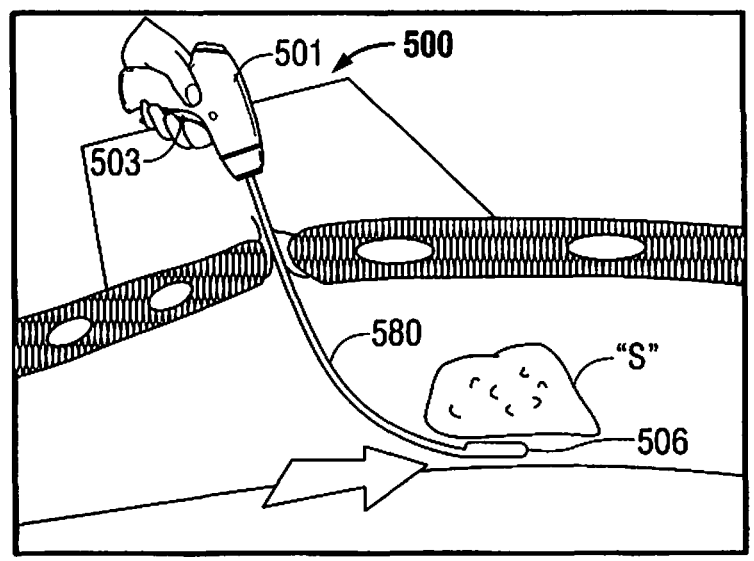
Figure 31C:
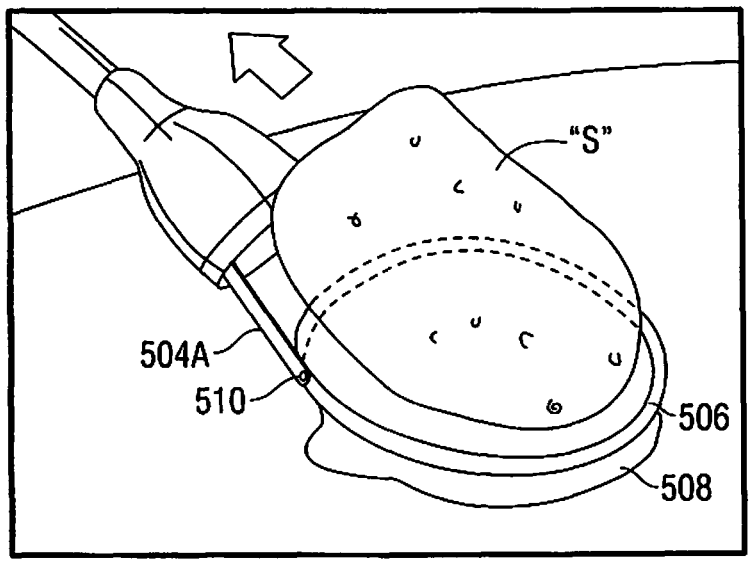
Figure 31D:
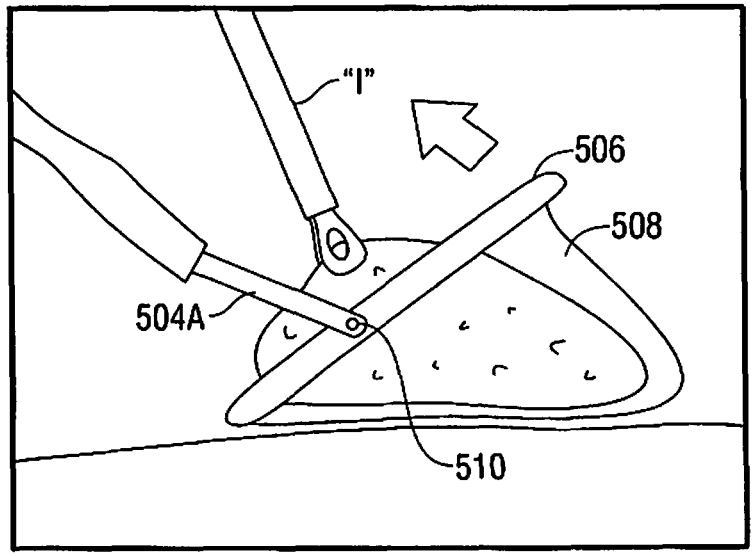
Figure 31E:
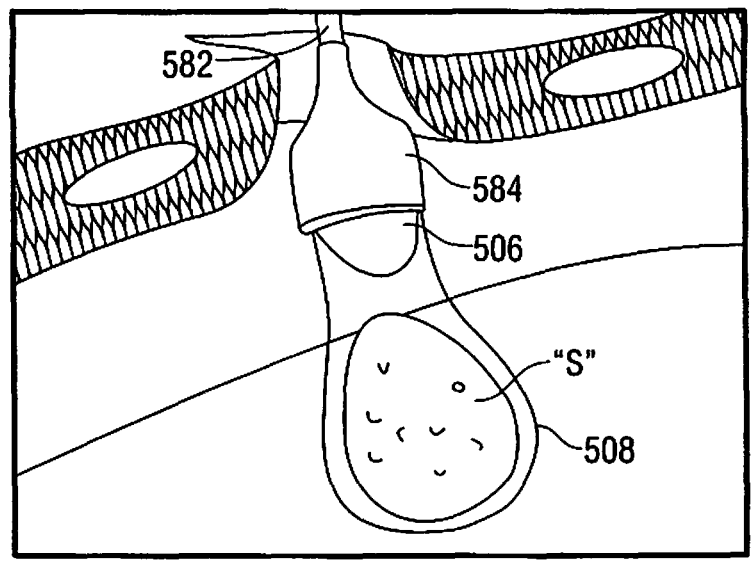
Figure 31F:
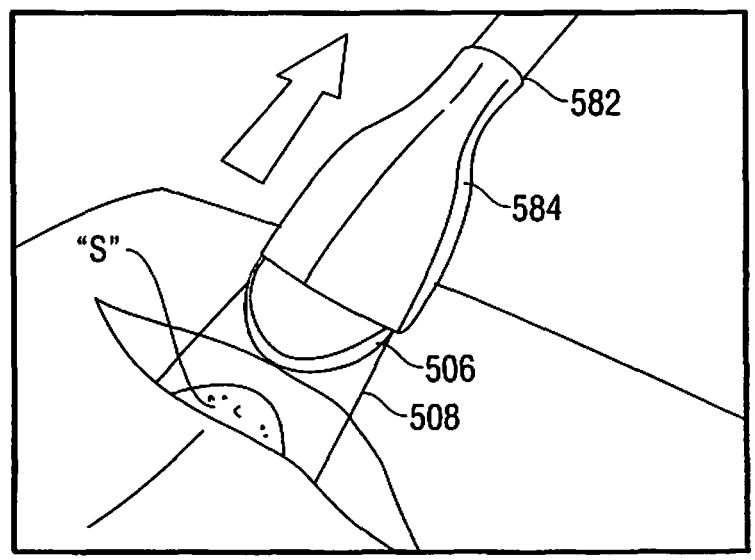

With reference to FIGS. 30-31F, and initially with reference to FIG. 30, another embodiment of the surgical retrieval apparatus is shown designated 500. Surgical retrieval apparatus 500 is substantially similar to the previously described surgical retrieval apparatus. More particularly, surgical retrieval apparatus 500 includes a housing 501 in the form of a handle assembly including a trigger mechanism 503 (FIG. 30), an elongated tubular member 580 and a drive rod 504 that is operably coupled to the trigger mechanism 503, and a support member 506 that is operably coupled to a pouch 508. Only those features that are unique to the surgical retrieval apparatus 500 are described in further detail.

Elongated tubular member 580 includes a proximal end that is operably coupled to the housing 501 and a distal end 582 that includes a flange 584 that is configured to house a portion of the drive rod 504 and/or support member 506 including the pouch 508. More particularly, the flange 584 is of suitable proportion and includes a generally flat "spatula" shape, see FIG. 31A. The "spatula" shape of the flange 584 facilitates insertion and removal of the distal end of the elongated tubular member 580. The flange 584 also allows space to house a larger bag and to enable sliding underneath the tissue specimen. In certain embodiments, the flange 584 may be removably coupled to the distal end 582 of the elongated tubular member 580. The configuration of the apparatus 500 allows the pouch 508 to be deployed beyond and under the tissue specimen, tipped back towards the incision and scoop the tissue specimen from beyond.

Drive rod 504 includes a proximal end that operably couples to the trigger mechanism 503 that is configured to impart axial movement the drive rod 504 within the elongated tubular member 580 upon actuation of the trigger mechanism 503. Drive rod 504 includes a distal end having two fingers 504a and 504b that are operably coupled to the support member 506. More particularly, the two fingers 504a and 504b are hinged to the support member 506 via one or more pivot pins 510 (or other suitable device). In the illustrated embodiment, each of the fingers 504a and 504b is coupled to the support member 506 via a respective pivot pin 510. The configuration of pivot pins 510 and fingers 504a and 504b facilitates moving the support member 506 including pouch 508 from a retracted position within the flange 584 (FIG. 31A) to a deployed position external the flange 584 (FIGS. 31C and 31D). Likewise, the configuration of pivot pins 510 and fingers 504a and 504b facilitates in moving the support member 506 including pouch 508 from the deployed position external the flange 584 (FIGS. 31C and 31D) to the retracted position within the flange 584 (FIG. 31A).

Support member 506 is of generally rigid construction and is configured to pivotably support the pouch 508. More particularly, and as noted above, support member 506 is hinged to the drive rod 504 via pivot pins 510. In accordance with the present disclosure, the support member 506 is configured to provide a point pivot about the pivot pins 510 after a tissue specimen "S" is positioned within the pouch 508 such that the support member 506 substantially aligns with the fingers 504a and 504b, see FIG. 31C. In the aligned position, the support member 506 including pouch 508 may be returned to the retracted position. As with the configuration of the support member 406 and pouch 408, support member 506 and pouch 508 are fixedly coupled or secured to one another by one or more suitable coupling or securement methods.

In use, elongated tubular member 580 is positioned within a thoracic cavity of a patient (FIG. 31A). Subsequently, support member 506 including pouch 508 is deployed from within the elongated tubular member 580 via a trigger mechanism 503 (FIG. 31B). After the support member 506 and the pouch 508 are properly positioned within the thoracic cavity of the patient, e.g., adjacent a tissue specimen "S," the specimen is placed within the pouch 508 (FIGS. 31C and 31D) via one or more suitable surgical instruments "I". The combination of positioning the tissue specimen "S" within the pouch 508 and retracting the drive rod 504 causes the support member 506 to pivot about the pivot pins 510 such that the support member 506 substantially aligns with the finger 504a and 504b. In the aligned position, and with continued retraction of the drive rod 504, the support member 506 (or portion thereof) is returned to the flange 584. Once the support member 506 and/or pouch 508 are in the confines of the flange 484, the tissue specimen is substantially prevented from dislodging from the pouch 508. Thereafter, the elongated tubular member 580 including support member 506 and pouch 508 are removed from the thoracic cavity (FIGS. 31E and 31F).

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical retrieval apparatus comprising:
   an elongated tubular member;
   a drive member slidably disposed in the elongated tubular member, a support member coupled to the drive member, the support member movable between a proximal position and a distal position at least partially exterior to the elongated tubular member in response to axial movement of the drive member and movable between a first condition and a second expanded condition;
   a pouch extending from the support member, the pouch having a first end and a closed second end, the first end transitionable between open and closed configurations when the support member transitions between the first condition and the second expanded condition; and
   an extension tube directly attached to the exterior of the elongated tubular member at a distal end thereof, a distal end of the extension tube being articulable to allow the distal end of the extension tube to be maneuvered to a desired location during a surgical procedure to draw a tissue specimen towards the pouch for facilitating retrieval of the tissue specimen.

2. The surgical retrieval apparatus of claim 1, further comprising a handle assembly including a vacuum port, the vacuum port communicating with a channel in the extension tube.

3. The surgical retrieval apparatus of claim 1, wherein the support member has a channel to receive fluid therein to expand the support member.

4. The surgical retrieval apparatus of claim 3, further comprising a trigger mechanism actuable to introduce fluid into the channel of the support member.

5. The surgical retrieval apparatus of claim 3, wherein the support member is substantially M-shaped in configuration prior to introduction of the fluid into the channel of the support member.

6. The surgical retrieval apparatus of claim 1, wherein the pouch includes a textured surface on the interior thereof.

7. The surgical retrieval apparatus of claim 1, wherein the extension tube is positioned adjacent the second end of the pouch.

* * * * *